(12) United States Patent
De La Rosa et al.

(10) Patent No.: US 11,857,575 B2
(45) Date of Patent: Jan. 2, 2024

(54) MESENCHYMAL STEM CELL-DERIVED EXOSOMES AND THEIR USES

(71) Applicant: Takeda Pharmaceutical Company Limited, Osaka (JP)

(72) Inventors: Olga De La Rosa, Madrid (ES); Eleuterio Lombardo, Madrid (ES); Wilfried Dalemans, Leuven (BE); Javier Garcia Casado, Caceres (ES); Rebeca Blazquez Duran, Caceres (ES); Francisco Miguel Sanchez Margallo, Caceres (ES)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 377 days.

(21) Appl. No.: 15/772,668

(22) PCT Filed: Nov. 2, 2016

(86) PCT No.: PCT/EP2016/076462
§ 371 (c)(1),
(2) Date: May 1, 2018

(87) PCT Pub. No.: WO2017/076924
PCT Pub. Date: May 11, 2017

(65) Prior Publication Data
US 2018/0318354 A1 Nov. 8, 2018

Related U.S. Application Data

(63) Continuation-in-part of application No. 14/929,578, filed on Nov. 2, 2015, now abandoned.

(51) Int. Cl.
*A61K 35/02* (2015.01)
*A61K 9/127* (2006.01)
*A61K 9/50* (2006.01)
*C12N 15/62* (2006.01)
*A61P 29/00* (2006.01)
*A61P 37/06* (2006.01)
*A61K 45/06* (2006.01)
*A61K 35/35* (2015.01)
*A61K 31/519* (2006.01)
*A61K 31/4709* (2006.01)
*A61K 31/444* (2006.01)
*A61K 31/4439* (2006.01)
*A61K 31/5377* (2006.01)
*G01N 1/40* (2006.01)
*C12N 5/0775* (2010.01)
*A61K 35/12* (2015.01)
*A61K 35/28* (2015.01)

(52) U.S. Cl.
CPC .............. *A61K 35/28* (2013.01); *A61K 9/127* (2013.01); *A61K 9/5068* (2013.01); *A61K 31/444* (2013.01); *A61K 31/4439* (2013.01); *A61K 31/4709* (2013.01); *A61K 31/519* (2013.01); *A61K 31/5377* (2013.01); *A61K 35/35* (2013.01); *A61K 45/06* (2013.01); *A61P 29/00* (2018.01); *A61P 37/06* (2018.01); *C12N 15/625* (2013.01); *A61K 2035/122* (2013.01); *A61K 2035/128* (2013.01); *A61K 2300/00* (2013.01); *C12N 5/0667* (2013.01); *G01N 1/4077* (2013.01)

(58) Field of Classification Search
CPC ...... A61K 35/28; A61K 9/127; A61K 9/5068; A61K 31/4439; A61K 31/444; A61K 31/4709; A61K 31/519; A61K 31/5377; A61K 35/35; A61K 45/06; A61P 37/06; A61P 29/00
See application file for complete search history.

(56) References Cited

U.S. PATENT DOCUMENTS

| 2011/0003008 A1 | 1/2011 | Lim |
| 2015/0079046 A1 | 3/2015 | Sinden et al. |
| 2017/0189449 A1 | 7/2017 | Lim |

FOREIGN PATENT DOCUMENTS

| EP | 2687219 A1 * | 1/2014 | ............. A61K 35/28 |
| EP | 2877187 B1 * | 6/2019 | ......... A61K 31/7105 |
| JP | 2011513217 A | 4/2011 | |
| WO | WO03006057 A1 | 1/2003 | |
| WO | 03093801 A1 | 11/2003 | |
| WO | WO-2009/105044 A1 * | 8/2009 | |
| WO | WO-2013/150303 A1 * | 10/2013 | |
| WO | WO-2014/013029 A1 * | 1/2014 | |
| WO | WO-2015/061568 A1 * | 4/2015 | |

OTHER PUBLICATIONS

Katsuda et al., "Human adipose tissue-derived mesenchymal stem cells secrete functional neprilysin-bound exosomes", 2013, Scientific Reports 3, p. 1-11.*
Katsuda et al., "Human adipose tissue-derived mesenchymal stem cells secrete functional neprilysin-bound exosomes", 2013, Nature: Scientific Reports 3, p. 1-11.*
Liang J, Zhang H, Wang D, Feng X, Wang H, Hua B, Liu B, Sun L. Allogeneic mesenchymal stem cell transplantation in seven patients with refractory inflammatory bowel disease. Gut. Mar. 1, 2012;61(3):468-9 (Year: 2012).*
Blazquez R, Sanchez-Margallo FM, de la Rosa O, Dalemans W, Álvarez V, Tarazona R, Casado JG. Immunomodulatory potential of human adipose mesenchymal stem cells derived exosomes on in vitro stimulated T cells. Frontiers in immunology. Nov. 4, 2014;5: 556;cited in IDS filed in IFW on Jul. 25, 2018. (Year: 2014).*

(Continued)

*Primary Examiner* — Allison M Fox
*Assistant Examiner* — Jennifer S Spence
(74) *Attorney, Agent, or Firm* — Greer, Burns & Crain, Ltd.

(57) ABSTRACT

The invention relates to exosomes derived from mesenchymal stem cells and well as isolated populations of said exosomes and method for preparing said isolated exosome populations. The invention also relates to a pharmaceutical composition comprising said exosome or isolated exosome population and their use in a method of treating an immune-mediated inflammatory disease in a subject.

5 Claims, 13 Drawing Sheets

(56) References Cited

OTHER PUBLICATIONS

Mokarizadeh A, Delirezh N, Morshedi A, Mosayebi G, Farshid AA, Mardani K. Microvesicles derived from mesenchymal stem cells: potent organelles for induction of tolerogenic signaling. Immunology letters. Sep. 1, 2012;147(1-2):47-54. (Year: 2012).*
Gonzalez-Rey E, Anderson P, González MA, Rico L, Büscher D, Delgado M. Human adult stem cells derived from adipose tissue protect against experimental colitis and sepsis. Gut. Jul. 1, 2009;58(7):929-39. (Year: 2009).*
Kim JY, Jeon HB, Yang YS, Oh W, Chang JW. Application of human umbilical cord blood-derived mesenchymal stem cells in disease models. World journal of stem cells. Apr. 26, 2010;2(2):34. (Year: 2010).*
Vlassov AV, Magdaleno S, Setterquist R, Conrad R. Exosomes: current knowledge of their composition, biological functions, and diagnostic and therapeutic potentials. Biochimica et Biophysica Acta (BBA)-General Subjects. Jul. 1, 2012;1820(7):940-8. (Year: 2012).*
Yeo RW, Lai RC, Tan KH, Lim SK. Exosome: a novel and safer therapeutic refinement of mesenchymal stem cell. Exosomes and Microvesicles. Jan. 1, 2013;1:7. (Year: 2013).*
Coussens LM, Werb Z. Inflammation and cancer. Nature. Dec. 2002;420(6917):860-7. (Year: 2002).*
Varga J, Pasche B. Anti-TGF-β therapy in fibrosis: recent progress and implications for systemic sclerosis. Current opinion in rheumatology. Nov. 2008;20(6):720. (Year: 2008).*
Fuschiotti P. Current perspectives on the immunopathogenesis of systemic sclerosis. ImmunoTargets and therapy. Apr. 2016;5:21. (Year: 2016).*
Christopeit M, Schendel M, Föll J, Müller LP, Keysser G, Behre G. Marked improvement of severe progressive systemic sclerosis after transplantation of mesenchymal stem cells from an allogeneic haploidentical-related donor mediated by ligation of CD137L. Leukemia. May 2008;22(5):1062-4. (Year: 2008).*
Lai RC, Arslan F, Lee MM, Sze NS, Choo A, Chen TS, Salto-Tellez M, Timmers L, Lee CN, El Oakley RM, Pasterkamp G. Exosome secreted by MSC reduces myocardial ischemia/reperfusion injury. Stem cell research. May 1, 2010;4(3):214-22 (Year: 2010).*
Oñate B, Vilahur G, Ferrer-Lorente R, Ybarra J, Díez-Caballero A, Ballesta-López C, Moscatiello F, Herrero J, Badimon L. The subcutaneous adipose tissue reservoir of functionally active stem cells is reduced in obese patients. The FASEB Journal. Oct. 2012;26(10):4327-36 (Year: 2012).*
Kordelas L, Rebmann V, Ludwig AK, Radtke S, Ruesing J, Doeppner TR, Epple M, Horn PA, Beelen DW, Giebel B. MSC-derived exosomes: a novel tool to treat therapy-refractory graft-versus-host disease. Leukemia. Apr. 2014;28(4):970-3 (Year: 2014).*
Strioga M, Viswanathan S, Darinskas A, Slaby O, Michalek J. Same or not the same? Comparison of adipose tissue-derived versus bone marrow-derived mesenchymal stem and stromal cells. Stem cells and development. Sep. 20, 2012;21(14):2724-52 (Year: 2012).*
Henkin J, Volpert OV. Therapies using anti-angiogenic peptide mimetics of thrombospondin-1. Expert opinion on therapeutic targets. Dec. 1, 2011;15(12):1369-86 (Year: 2011).*
Ringden O, Le Blanc K. Mesenchymal stem cells for treatment of acute and chronic graft-versus-host disease, tissue toxicity and hemorrhages. Best practice & research Clinical haematology. Mar. 1, 2011;24(1):65-72. (Year: 2011).*
Gonzalez-Rey, E., Anderson, P., González, M. A., Rico, L., Büscher, D., & Delgado, M. (2009). Human adult stem cells derived from adipose tissue protect against experimental colitis and sepsis. Gut, 58(7), 929-939. (Year: 2009).*
Alvarez, V. et al., "The Immunomodulatory Activity of Extracellular Vesicles Derived from Endometrial Mesenchymal Stem Cells on CD4+ T Cells is Partially Mediated by TGFbeta", Journal of Tissue Engineering and Regenerative Medicine, Aug. 19, 2018, pp. 2088-2098, vol. 12.

Schon, H. et al., "Immunomodulatory effects of transforming growth factor-B in the liver", Hepatobiliary Surgery and Nutrition, Dec. 2014, pp. 386-406, vol. 3, No. 6.
European Communication dated Sep. 22, 2020 for EP Application No. 16808572.8.
Alcayaga-Miranda, F. et al., "Combination Therapy of Menstrual Derived Mesenchymal Stem Cells and Antibodics Ameliorates Survival in Sepsis", Stem Cell Research and Therapy, Oct. 16, 2015, pp. 1-13, vol. 6, No. 99.
Alvarez, V. et al., "Comparative study of isolated human mesenchymal stemp cell derived exosomes for clinical use", Acta Bioquimica Clinica Latinoamericana, Sep. 2015, pp. 311-320, vol. 49, No. 3.
Peche, H. et al., "Induction of Tolerance by Exosomes and Short-Term Immunosuppression in a Fully MHC-Mismatched Rat Cardiac Allograft Model", American Journal of Transplantation, 2006, pp. 1541-1550, vol. 6.
Navarro, P. et al., "A Refined Method to Calculate False Discovery Rates for Peptide Identification Using Decoy Databases", Journal of Proteome Research, 2009, pp. 1792-1796, vol. 8.
Geginat, J. et al., "Proliferation and differentiation potential of human CD8+ memory T-cell subsets in response to antigen or homeostatic cytokines", Blood, Jun. 2003, No. 11, pp. 4260-4266, vol. 101.
Blazquez, R. et al., "Immunomodulatory potential of human adipose mesenchymal stem cells derived exosomes on in vitro stimulated T cells", Frontiers in Immunology, Nov. 2014, Article 556, 9 pages, vol. 5.
Bonzon-Kulichenko, E. et al., "A Robust Method for Quantitative High-throughput Analysis of Proteomes by 18O Labeling", Mol. Cell. Proteomics, 2011, 10(1):M110.003335. DOI: 10.1074/mcp.M110.003335.
Peche, H. et al., "Presentation of Donor Major Histocompatibility Complex Antigens by Bone Marrow Dendritic Cell-Derived Exosomes Modulates Allograft Rejection", Transplantation, Nov. 2003, No. 10, pp. 1503-1510, vol. 76.
Alcayaga-Miranda, F. et al., "Combination Therapy of Menstrual Derived Mesenchymal Stem Cells and Antibodics Ameliorates Survival in Sepsis", Stem Cell Research and Therapy, 2015, 6:199, pp. 1-13.
Xue, D. et al., "Endometrial Mesenchymal Stem Cells Isolated from Menstrual Blood by Adherence", Stem Cells International, Article ID 3573846, pp. 1-8, vol. 2016.
Rossignoli, F. et al., "Isolation, Characterization, and Transduction of Endometrial Decidual Tissue Multipotent Mesenchymal Stromal/Stem Cells from Menstrual Blood", BioMed Research International, Article ID 901821, pp. 1-15, vol. 2013.
Katsuda T. et al., "Human Adipose tissue-derived mesenchymal stem cells secrete functional neprilysin-bound exosomes", Scientific Reports, (2013), pp. 1-11, 3: 1197; DOI 10. 1038/srep01197.
Lin R. et al., "Exosomes from human adipose-derived mesenchymal stem cells promote migration through Wnt signaling pathway in a breast cancer cell model", Molecular Cell Biochem, (2013), pp. 13-20, vol. 383.
Alnarez, V. et al., "Comparative study of isolated human mesenchymal stemp cell derived exosomes for clinical use", Acta Bioquimica Clinica Latinoamericana, 2015, pp. 311-320, vol. 49 (3).
Japanese Office Action dated Oct. 23, 2020 for Japanese Application No. 2018-522514.
Igaku, Kitasato Medical, 2013, pp. 9-22, vol. 43.
Japanese Office Action dated Jun. 7, 2021 for Japanese Application No. 2018-522514.
Johansson, U., et al., "CD47 Ligation Induces a Rapid Caspase-Independent Apoptosis-Like Cell Death in Human Monocytes and Dendritic Cells", Scandinavian Journal of Immunology, pp. 40-49, No. 59.
Yu, H., et al., "Human Adipose Mesenchymal Stem Cell-derived Exosomes Protect Mice from DSS-Induced Inflammatory Bowel Disease by Promoting Intestinal-stem-cell and Epithelial Regeneration", Aging and Disease, Sep. 2021, pp. 1423-1437, vol. 12, No. 6.

* cited by examiner

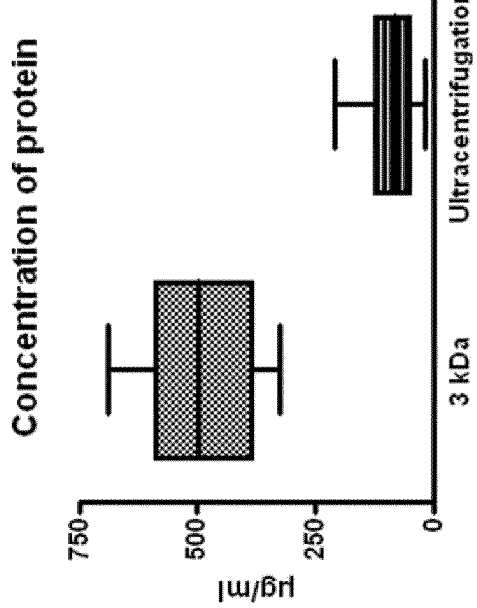
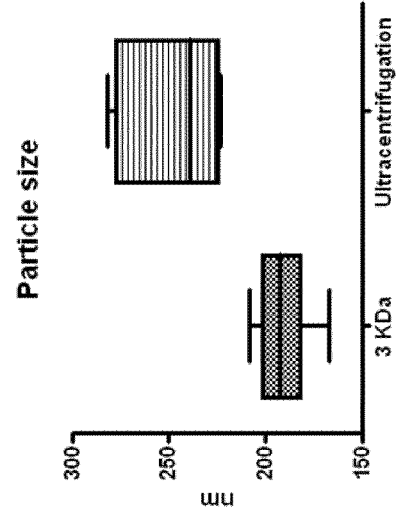
|  | 3 kDa | Ultracentrifugation |
|---|---|---|
| Minimum | 325,17 | 18,00 |
| 25% Percentile | 381,50 | 49,03 |
| Median | 499,29 | 79,50 |
| 75% Percentile | 586,34 | 123,50 |
| Maximum | 687,48 | 208,00 |
| Mean | 490,43 | 90,40 |
| Std. Deviation | 121,63 | 57,16 |
| Std. Error | 45,97 | 15,28 |
| Lower 95% CI of mean | 377,95 | 57,39 |
| Upper 95% CI of mean | 602,92 | 123,41 |
FIG. 6
|  | 3 kDa | Ultracentrifugation |
|---|---|---|
| Minimum | 167,00 | 223,00 |
| 25% Percentile | 181,00 | 224,00 |
| Median | 192,50 | 239,00 |
| 75% Percentile | 201,50 | 277,50 |
| Maximum | 208,00 | 282,00 |
| Mean | 191,08 | 246,83 |
| Std. Deviation | 13,48 | 25,06 |
| Std. Error | 3,89 | 10,23 |
| Lower 95% CI of mean | 182,52 | 220,54 |
| Upper 95% CI of mean | 199,65 | 273,13 |
FIG. 7

|  | 3 kDa | Ultracentrifugation |
|---|---|---|
| Minimum | 6,40 | 8,44 |
| 25% Percentile | 8,87 | 8,46 |
| Median | 13,00 | 9,27 |
| 75% Percentile | 14,70 | 9,59 |
| Maximum | 15,28 | 9,70 |
| Mean | 11,83 | 9,11 |
| Std. Deviation | 3,46 | 0,53 |
| Std. Error | 1,00 | 0,22 |
| Lower 95% CI of mean | 9,64 | 8,55 |
| Upper 95% CI of mean | 14,03 | 9,67 |

MESENCHYMAL STEM CELL-DERIVED EXOSOMES AND THEIR USES

FIELD OF THE INVENTION

The invention relates to exosomes derived from mesenchymal stem cells as well as to their use for the treatment immune-mediated inflammatory diseases.

BACKGROUND OF THE INVENTION

Exosomes are small membranous vesicles secreted by most cell types. These vesicles participate in cell-cell communication and their content consists of RNA, lipids, and proteins. Some of these proteins (i.e., CD9, CD63, or CD81) are ubiquitously expressed, but depending on the cell source, cell type-specific proteins can be found being responsible of their functionality. The proteins, lipids, and RNA expression of exosomes from different cells and organisms are extensively described in ExoCarta database.

Exosomes can be easily isolated by ultracentrifugation from in vitro cultured cells but different isolation protocols have been described in the literature. All these protocols differ from each other on the basis of particular types of research being divided as procedures for discovery, diagnostic, or preparative research. For a clinical-grade production of exosomes, safe technologies for large scale production are an absolute prerequisite.

In preclinical settings, especially in murine models, exosomes have been applied for the treatment of many different diseases such as infections, allergies as well as autoimmune diseases. Regarding the immunomodulatory potential of these vesicles, the first in vivo studies were conducted by Pêche et al. using bone marrow dendritic cell-derived exosomes (Pêche H. et al., Transplantation 2003, 76: 1503-10; Pêche H. et al., Am. J. Transplant. 2006, 6:1541-50). Compared to preclinical studies, only a few clinical trials have been conducted using exosomes. Some of the first clinical trials were conducted in cancer patients using dendritic cell-derived exosomes and ascites-derived exosomes where the safety, tolerability, and efficacy of the treatments were demonstrated.

At the present, the therapeutic potential of exosomes derived from MSCs (Exo-MSCs) has been successfully applied in murine models for the treatment of cardiovascular diseases. In this sense, the proangiogenic effect described in different stem cell subsets may be the responsible of this therapeutic effect.

There are no differences in terms of morphological features, isolation, and storage conditions between exosomes derived from MSCs and other sources. As to the identification, exo-MSCs express not only the common surface markers of exosomes, such as CD9 and CD81, but also some adhesion molecules, including CD29, CD44, and CD73, which are expressed on the membrane of MSCs.

Accumulative evidences have established that, the effect of MSC transplantation is thought to be mediated in part, by a paracrine effect. Indeed, in the context of myocardial infarct it was experimentally quantified that the overall beneficial effect of paracrine mechanisms accounted between 50 and 80%. Several advantages of using released factors from MSCs have been described. For example, transferred cells may die or not fully home into the site of damaged tissue whereas biological factors can be locally administered with a controlled dosage.

BRIEF DESCRIPTION OF THE INVENTION

The authors of the present invention have discovered that exosome populations isolated from human adipose mesenchymal stem cells have immunomodulatory properties that make them useful for the treatment of immunological diseases, in particular, they exert and inhibitory effect in the differentiation and activation of T cells (FIGS. 3 and 4) and a reduced proliferation (FIG. 2) and IFN-γ release on in vitro expanded T cells (FIG. 5).

Thus, in a first aspect, the invention relates to an exosome derived from mesenchymal stem cells (MSCs) characterised in that:
 it has a molecular weight of at least about 3 kDa, and/or
 it has a diameter between about 150 and about 300 nm and/or
 it comprises thrombospondin-1 (TSP-1)) and/or
 show low TGF-β and/or low latent TGF-β levels.

In a second aspect, the invention relates to an isolated exosome population derived from MSCs, characterised in that:
 at least 20% of the exosomes have an average molecular weight of at least about 3 kDa, and/or
 at least 20% of the exosomes have an average diameter between about 150 and about 300 nm and/or
 the exosomes from said population comprise TSP-1 and/or
 the exosomes show low TGF-β and/or low latent TGF-β levels In a third aspect, the invention relates to a method for preparing an isolated exosome population derived from MSCs comprising:
 a) filtering a cell-free MSC-conditioned medium using a 3 kDa cut-off membrane and recovering the retentate, or
 b) centrifuging a cell-free MSC-conditioned medium at a speed sufficient to precipitate exosomes and recovering the pellet.

In a fourth aspect, the invention relates to an isolated exosome population derived from MSCs obtained by the method of the third aspect.

In a fifth aspect, the invention relates to a composition comprising an isolated exosome population according to the second of fourth aspects of the invention in combination with a TGF-β inhibitor.

In a sixth aspect, the invention relates to a pharmaceutical composition comprising the exosome of the first aspect or the isolated exosome population of the second or fourth aspects of the invention.

In a seventh aspect, the invention relates to a method of treating an immune-mediated inflammatory disease in a subject suffering from said disease, which comprises administering to said subject a therapeutically effective amount of the exosome of the first aspect, of the isolated exosome population of the second or fourth aspects of the invention of a composition comprising an exosome population according to the invention and a TGF-β inhibitor according to the fifth aspect or the pharmaceutical composition according to the sixth aspect of the present invention.

BRIEF DESCRIPTION OF THE FIGURES

FIG. 6. Measurement of total protein concentration in exosomes isolated by different methods. Total protein concentration was determined by the Bradford method. Absorbance values were extrapolated from a standard curve of bovine serum albumin. The asterisks indicate statistically significant differences between groups (p≤0.05).

FIG. 7.—Determination of particle sizes in the samples. The graph and table show the graphical and statistical representation of the measurements. The asterisks indicate statistically significant differences between groups (p≤0.05).

DETAILED DESCRIPTION OF THE INVENTION

Exosomes

Figure 1A:
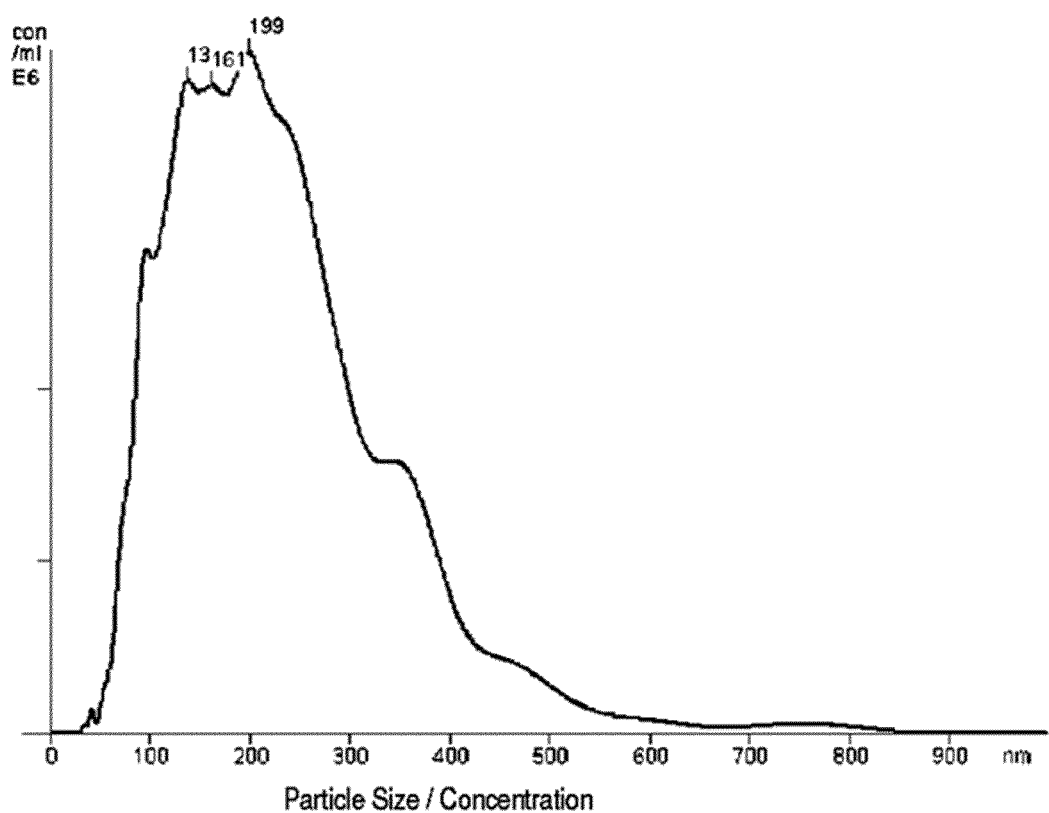
FIG. 1. A) Frequency size distribution graph of exo-hASCs. The nanoparticle tracking analysis was performed on exosome samples to quantify size distribution and particle concentration (nD6). A representative graph of nanoparticle tracking analysis is shown. B) Proteins identified in the exo-hASCs. Samples were separated by SDS-polyacrylamide gel. Proteins were visualized with Coomassie blue, and the bands were cut and digested. Resulting peptides were analysed by LC-MS/MS. Protein identification was performed using SEQUEST and SwissProt database.

In a first aspect, the invention relates to an exosome derived from mesenchymal stem cells (MSCs), hereinafter exosome of the first aspect, characterised in that:
it has a molecular weight of at least about 3 kDa, and/or
it has a diameter between about 150 and about 300 nm and/or
it comprises thrombospondin-1 (TSP-1) and/or
it has low TGF-β and/or low latent TGF-β levels.

The term "exosome", as used herein, refers to a cell-derived membranous vesicle. Exosomes are released from most cell types and can be found in many biological fluids. The exosome of the first aspect is derived from mensenchymal stem cells.

The term "mesenchymal stem cell" or "MSC", as used herein, refers to a multipotent somatic stem cell derived from mesoderm, having self-regenerating and differentiating capacity to produce progeny cells with a large phenotypic variety, including connective tissues, stroma of bone marrow, adipocytes, dermis and muscle, and menstrual tissue among others. MSCs generally have a cell marker expression profile characterized in that they are negative for the markers CD19, CD45, CD14 and HLA-DR, and positive for the markers CD105, CD106, CD90 and CD73.

The MSCs used in the present invention are preferably characterised in that (i) they do not express markers specific for antigen presenting cells, (ii) they do not express IDO (Indoleamine 2,3-Dioxygenase) constitutively, (iii) they express IDO upon stimulation with IFN-gamma, and (iv) they present the capacity to be differentiated into at least two cell lineages. Alternatively, the MSCs used in the present invention are preferably characterised by the presence and absence of a set of markers, namely, said cells are characterised in that (i) they express CD9, CD10, CD13, CD29, CD44, CD49a, CD51, CD54, CD55, CD58, CD59, CD90 or CD105, and (ii) they do not express CD11b, CD14, CD15, CD16, CD31, CD34, CD45, CD49f, CD102, CD104, CD106 or CD133.

MSCs may be isolated from any type of tissue. Generally MSCs will be isolated from bone marrow, adipose tissue, umbilical cord, peripheral blood or menstrual tissue. In a particular embodiment, the MSC are adipose tissue-derived stem cells.

The term "adipose tissue-derived stem cells" or "ASC", as used herein, refers to a MSC derived from adipose tissue. ASC can be isolated from adipose tissue by methods known in the art, for example the method described below under "Human adipose mesenchymal stem cells isolation and expansion". By "adipose tissue" it is meant any fat tissue. The adipose tissue may be brown or white adipose tissue, derived from, for example, subcutaneous, omental/visceral, mammary, gonadal, periorgan or other adipose tissue site. Preferably, the adipose tissue is subcutaneous white adipose tissue. The adipose tissue may comprise a primary cell culture or an immortalized cell line. The adipose tissue may be from any organism having fat tissue. In some embodiments, the adipose tissue is mammalian, and in further embodiments the adipose tissue is human. A convenient source of adipose tissue is liposuction surgery. However, it will be understood that neither the source of adipose tissue nor the method of isolation of adipose tissue is critical to the invention. In a particular embodiment, ASC are isolated from a lipoaspirate of a subject.

The term "menstrual tissue", as used herein, refers to a mucosal deriving from the inner lining of the uterus and which is discharged through the vagina during the menstruation and is usually composed of parts of uterine tissue as they exist immediately prior to menses, cells from the mucus lining of the vagina and bacteria making up the vaginal flora. Methods for the isolation of MSCs from menstrual tissue are well known in the art (see, e.g. Rossignioli et al., Biomed Res Int. 2013; 2013: 901821; Xu et al., Stem Cells International, 2016, 2016: 3573846; Alcayaga-Miranda et al., Stem Cell Research & Therapy, 20156:32.

The MSC can derived from any animal, preferably a mammal including a non-primate (e g, a cow, pig, horse, cat, dog, rat, or mouse) and a primate (e g, a monkey, or a human). In a particular embodiment, the MSC are human.

The exosome of the first aspect is characterized by one or more of the following features:
 it has a molecular weight of at least about 3 kDa, and/or
 it has a diameter between about 150 and about 300 nm and/or
 it comprises thrombospondin-1 (TSP-1) and/or
 it has low TGF-β and/or low latent TGF-β levels.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

(a) Molecular Weight of at Least about 3 kDa

The term "molecular weight" as used herein, refers to the sum of the atomic weights of all the atoms in a molecule. The molecular weight of the exosome of the first aspect is therefore the sum of the atomic weights of all the atoms in the molecules comprised in said exosome. The molecular weight of an exosome can be determined by means of a membrane with a particular cut-off. As the skilled person will understand, if a sample containing exosomes is passed through a 3 kDa cut-off membrane, the exosomes present in the resulting retentate will have a molecular weight of 3 kDa or more, while the exosomes included in the eluate will have a molecular weight of less than 3 kDa. In a particular embodiment, the exosome of the first aspect has a molecular weight of at least about 3 kDa, for example, at least about 5, at least about 10, at least about 20, at least about 30, at least about 40, at least about 50, at least about 75, at least about 100 kDa.

(b) Diameter Between about 150 and about 300 nm

The term "diameter", as used herein, refers to the maximum dimension of the exosome, it being understood that the exosome is not necessarily spherical. The diameter may be conveniently measured using conventional techniques for measuring nanoparticle size, such as microscopy techniques, for example transmission electron microscopy, or light scattering techniques. In a particular embodiment, the diameter of the exosome of the first aspect can be measured using the Nanoparticle Tracking Analysis (NTA), which is based on the analysis of both light scattering and Browian motion, as described in WO03/093801.

In a particular embodiment, the exosome of the first aspect has a diameter between about 223 and about 300 nm. In a more particular embodiment, the diameter is between about 170 and about 283 nm. In a more particular embodiment, the diameter is about 150 and about 193.5 nm.

(c) Presence of Thrombospondin-1 (TSP-1)

The term "thrombospondin-1" or "TSP-1" or "THBS1", as used herein, refers to a glycoprotein that mediates cell-to-cell and cell-to-matrix interactions. In humans it is encoded by the gene THBS1. The Apo C-I can be from any origin, for example human, bovine, murine, equine, canine, etc. In a particular embodiment, the TSP-1 is the human protein with the UniProt accession number P07996 (release of 16 Sep. 2015).

The presence of TSP-1 in an exosome can be determined by means of any method capable of detecting a particular protein in a sample. By way of a non-limiting illustration, the presence of TSP-1 can be determined by means of a technique which comprises the use of antibodies with the capacity for binding specifically to TSP-1 (or to fragments thereof containing the antigenic determinants), or alternatively by means of a technique which does not comprise the use of antibodies such as, for example, by techniques based on mass spectroscopy. The antibodies can be monoclonal, polyclonal or fragment thereof, Fv, Fab, Fab' and F(ab')2, scFv, diabodies, triabodies, tetrabodies and humanized antibodies. Similarly, the antibodies may be labeled. Illustrative, but non-exclusive, examples of markers that can be herein used include radioactive isotopes, enzymes, fluorophores, chemiluminescent reagents, enzyme cofactors or substrates, enzyme inhibitors, particles, or dyes. There is a wide variety of known test that can be used according for determining the presence of TSP-1 in an exosome, such as combined application of non-labeled antibodies (primary antibodies) and labeled antibodies (secondary antibodies), Western blot or immunoblot, ELISA (enzyme-linked immunosorbent assay), RIA (radioimmunoassay), competitive EIA (enzyme immunoassay), DAS-ELISA (double antibody sandwich ELISA), two-dimensional gel electrophoresis, capillary electrophoresis, immunocytochemical and immunohistochemical techniques, immunoturbidimetry, immunofluorescence, techniques based on the use of biochips or protein microarrays including specific antibodies or assays based on the colloidal precipitation in formats such as reagent strips and assays based on antibody-linked quantum dots.

(d) Low TGF-β and/or Low Latent TGF-β Levels

The term latent TGF-β levels, as used herein, refers to the levels of either Small Latent Complex (SLC), which is a complex of the TGF-β precursor molecule containing a propeptide region in addition to the TGF-β homodimer and the Latency Associated Peptide (LAP), which is a protein derived from the N-terminal region of the TGF-β gene product. In another embodiment, the term latent TGF-β levels refers to the Large Latent Complex (LLC), which is a complex comprising the Small Latent Complex (SLC) and the Latent TGF-β-Binding Protein (LTBP), preferably the LTBP-1, LTBP-2, LTBP-3 and LTBP-4. The attachment of TGF-β to the LTBP is by disulfide bond which allows it to remain inactive by preventing it from binding to its receptors.

In one embodiment, when the exosomes are derived from MSC derived from adipose tissue, their TGF-β content is preferably is between 0.001 and 0.5 μg TGF-β per μg of exosome, more preferably between 0.005 and 0.025 μg TGF-β per μg of exosome, even more preferably between 0.01 and 0.02 μg TGF-β per μg of exosome.

In another embodiment, the exosomes are derived from MSC derived from menstrual tissue and have a TGF-β content which is between 0.1 and 1 μg TGF-β per μg of exosome, more preferably between 0.2 and 0.8 μg TGF-β per μg of exosome, even more preferably between 0.3 and 0.7 μg TGF-β per μg of exosome or between 0.4 and 0.6 μg TGF-β per μg of exosome.

In one embodiment, when the exosomes are derived from MSC derived from adipose tissue, their latent TGF-β content is preferably is between 0.0001 and 0.01 μg latent TGF-β per μg of exosome, more preferably between 0.0005 and 0.005 μg of latent TGF-β per μg of exosome, even more preferably between 0.001 and 0.002 μg of latent TGF-β per μg of exosome.

In another embodiment, the exosomes are derived from MSC derived from menstrual tissue and have a latent TGF-β content which is between 0.001 and 0.5 μg latent TGF-β per μg of exosome, more preferably between 0.005 and 0.025 μg latent TGF-β per μg of exosome, even more preferably between 0.01 and 0.02 μg latent TGF-β per μg of exosome.

In a particular embodiment, the exosome of the first aspect has a molecular weight of at least about 3 kDa and a diameter between about 150 and about 300 nm.

In another particular embodiment, the exosome of the first aspect has a molecular weight of at least about 3 kDa and comprises TSP-1.

In another particular embodiment, the exosome of the first aspect has a diameter between about 150 and about 300 nm and comprises TSP-1.

In another particular embodiment, the exosome of the first aspect has a molecular weight of at least about 3 kDa, a diameter between about 150 and about 300 nm and comprises TSP-1.

Isolated Exosome Population

In a second aspect, the invention relates to an isolated exosome population derived from MSCs, characterised in that:
- at least 20% of the exosomes have an average molecular weight of at least about 3 kDa, and/or
- at least 20% of the exosomes have an average diameter between about 150 and about 300 nm and/or
- the exosomes from said population comprise TSP-1 and/or
- the exosomes show low TGF-β and/or low latent TGF-β levels.

The terms "exosome", "MSC", "molecular weight", "diameter", "about", "TSP-1", low TGF-β" or "low latent TGF-β have been previously defined in connection with the exosome of the first aspect.

In a particular embodiment, the MSCs are adipose tissue-derived stem cells (ASCs), preferably human ADSC. In another embodiment, the MSCs are derived from menstrual tissue, preferably human menstrual tissue.

The term "exosome population", as used herein, refers to a set formed at least by 2 exosomes, at least 5, at least 10, at least 50, at least 100, at least 500, at least 1000 or more exosomes.

The term "isolated exosome population", as used herein, refers to a population of exosomes, isolated from the human or animal body, which is substantially free of one or more exosome populations that are associated with said exosome population in vivo or in vitro. In a particular embodiment, the "isolated exosome population" is substantially free of cell or cellular debris, for example, substantially free of the cells from which said exosome population derives.

The isolated exosome population of the second aspect is characterized by one or more of the following features:
- at least 20% of the exosomes have an average molecular weight of at least about 3 kDa,
- at least 20% of the exosomes have an average diameter between about 150 and about 300 nm,
- the exosomes from said population comprise TSP-1.
- they contain low TGF-β or low latent TGF-β levels.

1. At Least 20% of the Exosomes have an Average Molecular Weight of at Least about 3 kDa The term "average molecular weight", as used herein, refers to the half-value molecular weight which is defined such that 50% of the exosomes of the population are below this molecular weight.

In a particular embodiment, at least 20%, at least 40%, at least 60%, at least 80%, at least 90%, at least 95% or at least 95% of the exosomes have an average molecular weight of at least about 3 kDa, for example at least about 3 kDa, for example, at least about 10, at least about 20, at least about 30, at least about 40, at least about 50, at least about 75, at least about 100 kDa.

In a particular embodiment, at least 20% of the exosomes have an average molecular weight of at least about 3 kDa. In another particular embodiment, at least 20% of the exosomes have an average molecular weight of at least about 10 kDa. In another particular embodiment, at least 20% of the exosomes have an average molecular weight of at least about 20 kDa. In another particular embodiment, at least 20% of the exosomes have an average molecular weight of at least about 30 kDa. In another particular embodiment, at least 20% of the exosomes have an average molecular weight of at least about 40 kDa. In another particular embodiment, at least 20% of the exosomes have an average molecular weight of at least about 50 kDa. In another particular embodiment, at least 20% of the exosomes have an average molecular weight of at least about 75 kDa. In another particular embodiment, at least 20% of the exosomes have an average molecular weight of at least about 100 kDa.

In a particular embodiment, at least 40% of the exosomes have an average molecular weight of at least about 3 kDa. In another particular embodiment, at least 40% of the exosomes have an average molecular weight of at least about 10 kDa. In another particular embodiment, at least 40% of the exosomes have an average molecular weight of at least about 20 kDa. In another particular embodiment, at least 40% of the exosomes have an average molecular weight of at least about 30 kDa. In another particular embodiment, at least 40% of the exosomes have an average molecular weight of at least about 40 kDa. In another particular embodiment, at least 40% of the exosomes have an average molecular weight of at least about 50 kDa. In another particular embodiment, at least 40% of the exosomes have an average molecular weight of at least about 75 kDa. In another particular embodiment, at least 40% of the exosomes have an average molecular weight of at least about 100 kDa.

In a particular embodiment, at least 60% of the exosomes have an average molecular weight of at least about 3 kDa.

In another particular embodiment, at least 60% of the exosomes have an average molecular weight of at least about 10 kDa. In another particular embodiment, at least 60% of the exosomes have an average molecular weight of at least about 20 kDa. In another particular embodiment, at least 60% of the exosomes have an average molecular weight of at least about 30 kDa. In another particular embodiment, at least 60% of the exosomes have an average molecular weight of at least about 40 kDa. In another particular embodiment, at least 60% of the exosomes have an average molecular weight of at least about 50 kDa. In another particular embodiment, at least 60% of the exosomes have an average molecular weight of at least about 75 kDa. In another particular embodiment, at least 60% of the exosomes have an average molecular weight of at least about 100 kDa.

In a particular embodiment, at least 80% of the exosomes have an average molecular weight of at least about 3 kDa. In another particular embodiment, at least 80% of the exosomes have an average molecular weight of at least about 10 kDa. In another particular embodiment, at least 80% of the exosomes have an average molecular weight of at least about 20 kDa. In another particular embodiment, at least 80% of the exosomes have an average molecular weight of at least about 30 kDa. In another particular embodiment, at least 80% of the exosomes have an average molecular weight of at least about 40 kDa. In another particular embodiment, at least 80% of the exosomes have an average molecular weight of at least about 50 kDa. In another particular embodiment, at least 80% of the exosomes have an average molecular weight of at least about 75 kDa. In another particular embodiment, at least 80% of the exosomes have an average molecular weight of at least about 100 kDa.

In a particular embodiment, at least 90% of the exosomes have an average molecular weight of at least about 3 kDa. In another particular embodiment, at least 90% of the exosomes have an average molecular weight of at least about 10 kDa. In another particular embodiment, at least 90% of the exosomes have an average molecular weight of at least about 20 kDa. In another particular embodiment, at least 90% of the exosomes have an average molecular weight of at least about 30 kDa. In another particular embodiment, at least 90% of the exosomes have an average molecular weight of at least about 40 kDa. In another particular embodiment, at least 90% of the exosomes have an average molecular weight of at least about 50 kDa. In another particular embodiment, at least 60% of the exosomes have an average molecular weight of at least about 75 kDa. In another particular embodiment, at least 90% of the exosomes have an average molecular weight of at least about 100 kDa.

In a particular embodiment, at least 95% of the exosomes have an average molecular weight of at least about 3 kDa. In another particular embodiment, at least 95% of the exosomes have an average molecular weight of at least about 10 kDa. In another particular embodiment, at least 95% of the exosomes have an average molecular weight of at least about 20 kDa. In another particular embodiment, at least 95% of the exosomes have an average molecular weight of at least about 30 kDa. In another particular embodiment, at least 95% of the exosomes have an average molecular weight of at least about 40 kDa. In another particular embodiment, at least 95% of the exosomes have an average molecular weight of at least about 50 kDa. In another particular embodiment, at least 60% of the exosomes have an average molecular weight of at least about 75 kDa. In another particular embodiment, at least 95% of the exosomes have an average molecular weight of at least about 100 kDa.

In a particular embodiment, at least 99% of the exosomes have an average molecular weight of at least about 3 kDa. In another particular embodiment, at least 99% of the exosomes have an average molecular weight of at least about 10 kDa. In another particular embodiment, at least 99% of the exosomes have an average molecular weight of at least about 20 kDa. In another particular embodiment, at least 99% of the exosomes have an average molecular weight of at least about 30 kDa. In another particular embodiment, at least 99% of the exosomes have an average molecular weight of at least about 40 kDa. In another particular embodiment, at least 99% of the exosomes have an average molecular weight of at least about 50 kDa. In another particular embodiment, at least 99% of the exosomes have an average molecular weight of at least about 75 kDa. In another particular embodiment, at least 99% of the exosomes have an average molecular weight of at least about 100 kDa.

2. At Least 20% of the Exosomes have an Average Diameter Between about 150 and about 300 nm The term "average molecular diameter", as used herein, refers to the half-value diameter which is defined such that 50% of the exosomes of the population are below this diameter.

In a particular embodiment, at least 20%, at least 40%, at least 60%, at least 80%, at least 90%, at least 95% or at least 95% of the exosomes have an average diameter between about 150 and about 300 nm, more particularly between about 223 and about 300 nm, even more particularly between about 150 and about 193.5 nm.

In a particular embodiment, at least 20% of the exosomes have an average diameter between about 150 and about 300 nm. In another particular embodiment, at least 20% of the exosomes have an average diameter between about 223 and about 300 nm. In another particular embodiment, at least 20% of the exosomes have an average diameter between about 150 and about 193.5 nm.

In a particular embodiment, at least 40% of the exosomes have an average diameter between about 150 and about 300 nm. In another particular embodiment, at least 40% of the exosomes have an average diameter between about 223 and about 300 nm. In another particular embodiment, at least 40% of the exosomes have an average diameter between about 150 and about 193.5 nm.

In a particular embodiment, at least 60% of the exosomes have an average diameter between about 150 and about 300 nm. In another particular embodiment, at least 60% of the exosomes have an average diameter between about 223 and about 300 nm. In another particular embodiment, at least 60% of the exosomes have an average diameter between about 150 and about 193.5 nm.

In a particular embodiment, at least 80% of the exosomes have an average diameter between about 150 and about 300 nm. In another particular embodiment, at least 80% of the exosomes have an average diameter between about 223 and about 300 nm. In another particular embodiment, at least 80% of the exosomes have an average diameter between about 150 and about 193.5 nm.

In a particular embodiment, at least 90% of the exosomes have an average diameter between about 150 and about 300 nm. In another particular embodiment, at least 90% of the exosomes have an average diameter between about 223 and about 300 nm. In another particular embodiment, at least 90% of the exosomes have an average diameter between about 150 and about 193.5 nm.

In a particular embodiment, at least 95% of the exosomes have an average diameter between about 150 and about 300 nm. In another particular embodiment, at least 95% of the exosomes have an average diameter between about 223 and about 300 nm. In another particular embodiment, at least 95% of the exosomes have an average diameter between about 150 and about 193.5 nm.

In a particular embodiment, at least 20% of the exosomes of the population of the second aspect have an average molecular weight of at least about 3 kDa and at least 20% of the exosomes of the population have an average diameter between about 150 and about 300 nm.

(3) Presence of Thrombospondin-1 (TSP-1)

The term "thrombospondin-1" or "TSP-1" or "THBS1", as used herein, refers to a glycoprotein that mediates cell-to-cell and cell-to-matrix interactions. In humans it is encoded by the gene THBS1. The Apo C-I can be from any origin, for example human, bovine, murine, equine, canine, etc. In a particular embodiment, the TSP-1 is the human protein with the UniProt accession number P07996 (release of 16 Sep. 2015).

The presence of TSP-1 in an exosome can be determined by means of any method capable of detecting a particular protein in a sample. By way of a non-limiting illustration, the presence of TSP-1 can be determined by means of a technique which comprises the use of antibodies with the capacity for binding specifically to TSP-1 (or to fragments thereof containing the antigenic determinants), or alternatively by means of a technique which does not comprise the use of antibodies such as, for example, by techniques based on mass spectroscopy. The antibodies can be monoclonal, polyclonal or fragment thereof, Fv, Fab, Fab' and F(ab')2, scFv, diabodies, triabodies, tetrabodies and humanized antibodies. Similarly, the antibodies may be labeled. Illustrative, but non-exclusive, examples of markers that can be herein used include radioactive isotopes, enzymes, fluorophores, chemiluminescent reagents, enzyme cofactors or substrates, enzyme inhibitors, particles, or dyes. There is a wide variety of known test that can be used according for determining the presence of TSP-1 in an exosome, such as combined application of non-labeled antibodies (primary antibodies) and labeled antibodies (secondary antibodies), Western blot or immunoblot, ELISA (enzyme-linked immunosorbent assay), RIA (radioimmunoassay), competitive EIA (enzyme immunoassay), DAS-ELISA (double antibody sandwich ELISA), two-dimensional gel electrophoresis, capillary electrophoresis, immunocytochemical and immunohistochemical techniques, immunoturbidimetry, immunofluorescence, techniques based on the use of biochips or protein microarrays including specific antibodies or assays based on the colloidal precipitation in formats such as reagent strips and assays based on antibody-linked quantum dots.

(4) Low TGF-β and/or Low Latent TGF-β Levels

The term latent TGF-β levels, as used herein, refers to the levels of either Small Latent Complex (SLC), which is a complex of the TGF-β precursor molecule containing a propeptide region in addition to the TGF-β homodimer and the Latency Associated Peptide (LAP), which is a protein derived from the N-terminal region of the TGFβ gene product. In another embodiment, the term latent TGF-β levels refers to the Large Latent Complex (LLC), which is a complex comprising the Small Latent Complex (SLC) and the Latent TGF-β-Binding Protein (LTBP), preferably the LTBP-1, LTBP-2, LTBP-3 and LTBP-4. The attachment of TGF-β to the LTBP is by disulfide bond which allows it to remain inactive by preventing it from binding to its receptors.

In one embodiment, the TGF-β can be TGFβ-1, TGFβ-2 or TGFβ-3 or any combination thereof.

In one embodiment, when the exosomes are derived from MSC derived from adipose tissue, their TGF-β content is preferably is between 0.001 and 0.5 ng TGF-β per µg of exosome, more preferably between 0.005 and 0.25 ng TGF-β per µg of exosome, even more preferably between 0.075 and 0.2 ng TGF-β per µg of exosome.

In another embodiment, the exosomes are derived from MSC derived from menstrual tissue and have a TGF-β content which is between 0.1 and 1 ng TGF-β per µg of exosome, more preferably between 0.2 and 0.8 ng TGF-β per µg of exosome, even more preferably between 0.3 and 0.7 ng TGF-β per µg of exosome or between 0.4 and 0.6 µg TGF-β per ng of exosome.

In one embodiment, when the exosomes are derived from MSC derived from adipose tissue, their latent TGF-β content is preferably is between 0.0001 and 0.02 ng latent TGF-β per µg of exosome, more preferably between 0.0005 and 0.01 ng of latent TGF-β per µg of exosome, even more preferably between 0.001 and 0.005 ng of latent TGF-β per µg of exosome.

In another embodiment, the exosomes are derived from MSC derived from menstrual tissue and have a latent TGF-β content which is between 0.001 and 0.5 ng latent TGF-β per µg of exosome, more preferably between 0.005 and 0.025 ng latent TGF-β per µg of exosome, even more preferably between 0.01 and 0.02 ng latent TGF-β per µg of exosome.

In one embodiment, the TGF-β or latent TGF-β content is provided in nanograms of TGF-β or latent TGF-β as the case may be per µg of exosome protein. In another embodiment, the TGF-β or latent TGF-β content is provided in nanograms of TGF-β or latent TGF-β as the case may be per µg of total exosome weight, i.e including both protein and lipids.

In another particular embodiment, at least 20% of the exosomes of the population of the second aspect have an average molecular weight of at least about 3 kDa and the exosomes of the population comprise TSP-1.

In another particular embodiment, at least 20% of the exosomes of the population of the second aspect have an average diameter between about 150 and about 300 nm and comprises TSP-1.

In another particular embodiment, at least 20% of the exosomes of the population of the second aspect have an average molecular weight of at least about 3 kDa, at least 20% of the exosomes of the population have an average diameter between about 150 and about 300 nm and the exosomes of the population comprise TSP-1.

Method for Preparing an Isolated Exosome Population Derived from MSCs and Isolated Exosome Population Obtained Thereby In a third aspect, the invention relates to a method for preparing an isolated exosome population derived from MSCs, hereinafter method of the third aspect, comprising:
a) filtering a cell-free MSC-conditioned medium using a 3 kDa cut-off membrane and recovering the retentate,
or
b) centrifuging a cell-free MSC-conditioned medium at a speed sufficient to precipitate exosomes and recovering the pellet.

The terms "isolated exosome population" and "MSC" have been previously defined in connection to the exosome of the first aspect of the invention.

In a particular embodiment, the MSCs are adipose tissue-derived stem cells (ASCs). In another aspect, the MSCs are MSCs derived from menstrual tissue.

In a particular embodiment, the MSCs are human.

The method of the third aspect comprises a first step of filtering a cell-free MSC-conditioned medium using a 3 kDa cut-off membrane.

The term "cell-free MSC-conditioned medium", as used herein, refers to a medium substantially free of cells which has been contacted with the MSC in culture. The term "medium" or "culture medium", as used herein, refers to any substance or preparation used for the cultivation of living cells, including the components of the environment surrounding the cells. The medium can be any medium adequate for culturing MSC, for example Dulbecco's Modified Eagle's Medium (DMEM), with antibiotics (for example, 100 units/ml Penicillin and 100 μg/ml Streptomycin) or without antibiotics, and 2 mM glutamine, and supplemented with 2%-20% fetal bovine serum (FBS). In a particular embodiment, the MSC-conditioned medium does not comprise any type of sera, including fetal bovine serum, bovine serum (BS), calf serum (CS), fetal calf serum (FCS), newborn calf serum (NCS), goat serum (GS), horse serum (HS), porcine serum, sheep serum, rabbit serum, rat serum (RS). In another particular embodiment, the MSC-conditioned medium comprises insulin-transferrin-selenium. In a more particular embodiment, the MSC-conditioned medium is DMEM containing 1% insulin-transferrin-selenium.

In a particular embodiment, the MSC-conditioned medium has been contacted with the MSC culture for at least 1 hour, at least 2 hours, at least 6 hours, at least 12 hours, at least 24 hours, at least 2 days, at least 3 days, at least 4 days, at least 5 days or more. In a more particular embodiment, the MSC-conditioned medium has been contacted with the MSCs for 3 or 4 days.

The cell-free MSC-conditioned medium can be obtained by any method known by the skilled person that allows recovering a culture medium without the cells. For example, the medium can be collected from a monolayer culture of MSCs.

In a particular embodiment, the cell-free MSC conditioned medium is obtained by collecting the medium from MSCs culture, centrifuging said medium in order to remove cells and debris and collecting the supernatant. In a more particular embodiment, cells and debris are removed by subjecting the medium to two successive centrifugations at 1000×g and 5000×g respectively. In an even more particular embodiment, these centrifugations are performed at 4° C. In a still more particular embodiment, the first centrifugation lasts about 10 minutes and the second centrifugation lasts about 20 minutes.

The first step of the method of the third aspect comprises filtering a cell-free MSC-conditioned medium using a 3 kDa cut-off membrane and recovering the retentate. The term "filtering", as used herein, means making the MSC-conditioned media to pass through the membrane. The term "3 kDa cut-off membrane", as used herein, refers to a porous plain sheet of a material having pores with a diameter which allows particles of less than 3 kDa to pass through but prevents particles of 3 kDa or more to pass through. The MSC-conditioned medium can be filtered with the 3 kDa cut-off membrane by any appropriate technique, for example, centrifuging the medium on centrifugal tubes provided with the 3 kDa cut-off membrane. The membrane can be of any suitable material, for example, cellulose.

The term "retentate", as used herein, refers to the portion of the medium which is not able to pass though the 3 kDa cut-off membrane.

The second step of the method of the third aspect comprises centrifuging the cell-free MSC-conditioned medium at a speed sufficient to precipitate exosomes and recovering the pellet.

The term "centrifuging", as used herein, refers to subjecting the cell-free MSC-conditioned medium to a centrifuge force in order to separate the components of said medium based on their different behaviour upon exerting said centrifugal force. The "speed sufficient to precipitate exosomes" is can be determined by the skilled person depending on the size of the exosomes. In a particular embodiment, the speed sufficient to precipitate exosomes is between 100,000 g and 1,000,000 g, and therefore, the centrifugation is an ultracentrifugation. In a more particular embodiment, the centrifugation is performed at 100000×g. In a particular embodiment, the centrifugation lasts between 30 minutes and 12 hours. In a more particular embodiment, the centrifugation lasts between 2 hour and 10 hours. In an even more particular embodiment the centrifugation lasts about 6 hours.

In a fourth aspect, the invention relates to the isolated exosome population derived from MSCs obtained by the method of the third aspect.

In a particular embodiment, the MSCs are adipose tissue-derived stem cells (ASCs).

In a particular embodiment, the MSCs are human.

Exosome-Containing Compositions According to the Invention and Uses Thereof

In a fifth aspect, the invention relates to a composition comprising an exosome population according to the second or fourth aspects of the present invention and a TGF-β inhibitor.

The terms "exosome", "isolated exosome population", "MSC", "molecular weight", "average molecular weight", "diameter", "average diameter", "about" and "TSP-1" have been previously defined in connection with the exosome of the first aspect of the invention and are equally applicable to the exosome-containing compositions as defined herein.

The "term TGF-β inhibitor", as used herein, is understood as any compound capable of preventing signal transduction caused by the interaction between TGF-β and its receptor. TGF-β inhibitors that can be used according to the present invention include compounds preventing the competitive or allosteric binding of TGF-β to its receptor, compounds binding to TGF-β and compounds inhibiting the intracellular signalling of TGF-β. Proper assays to determine the inhibitory capacity of a TGF-β inhibitor include the in vitro inhibition of TGF-β biological activity by using the inhibitor in My-1-Lu cell proliferation assays as well as the in vivo inhibition of TGF-β biological activity by the inhibitor using a model of acute liver damage induced by CCl4 (disclosed in WO200519244). For more details about TGF-β antagonists see also Wojtowicz-Praga (2003).

In one embodiment, the TGF-β inhibitor is a specific TGF-β1 inhibitor, a specific TGF-β2 inhibitor or a specific TGF-β3 inhibitor. In another embodiment, the TGF-β inhibitor is capable of inhibiting all TGF-β isoforms, including TGF-β1, TGF-β2 and TGF-β3.

TGF-β inhibitors are capable of preventing signal transduction caused by the interaction between TGF-β and its receptor by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100% (i.e., absent).

Suitable TGF-β inhibitors for use in the present invention are, without limitation, those defined in Table 1:

TABLE 1

| TGFbeta inhibitors. |
| --- |

1. The compound 2-(6-methyl-pyridin-2-yl)-3-[6-amido-quinolin-4-yl)-5,6-dihydro-4H-pyrrolo[1,2-b]pyrazole monohydrate (also known as LY2157299 monohydrate) having the structure

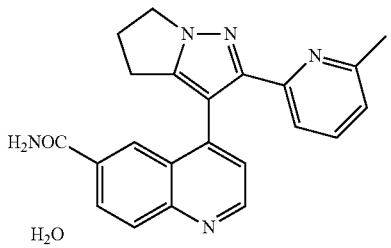 [SMILES: Cc1cccc(-c2nn3c(c2-c2ccnc4ccc(C(N)=O)cc24)CCC3)n1 ; O]

in a crystalline form and polymorphs, solvates or hydrates thereof.
2. Polymorphs, solvates or hydrates of tranilast (N-[3,4-dimethoxycinnamoyl]-anthranilic acid)
3. Polymorphs, solvates or hydrates of 4-(5-benzo(1,3)dioxol-5-yl-4-pyridin-2-yl-1H-imidazol-2-yl)benzamide (also known as SB-431542)
4. Polymorphs, solvates or hydrates of 4-[4-(3,4-Methylenedioxyphenyl)-5-(2-pyridyl)-1H-imidazol-2-yl]-benzamide hydrate
5. Polymorphs, solvates or hydrates of 4-[4-(1,3-Benzodioxol-5-yl)-5-(2-pyridinyl)-1H-imidazol-2-yl]-benzamide hydrate
6. Polymorphs, solvates or hydrates of NPC-30345
7. Polymorphs, solvates or hydrates of 4-(3-pyridin-2-yl-1H-Pyrazol-4-Yl)quinoline (also known as LY364947)
8. Polymorphs, solvates or hydrates of 3-(6-Methylpyridin-2-yl)-1-phenylthiocarbamoyl-4-quinolin-4-yl pyrazole (also known as A-83-01)
9. Polymorphs, solvates or hydrates of 2-(6-methyl-pyridin-2-yl)-3-[6-amino-quinolin-4-yl)-5,6-dihydro-4H-pyrrolo[1,2-b]pyrazole (also known as LY2157299)
10. Polymorphs, solvates or hydrates of LY550410
11. Polymorphs, solvates or hydrates of LY580276
12. Polymorphs, solvates or hydrates of LY566578
13. Polymorphs, solvates or hydrates of LY2109761 having the structure

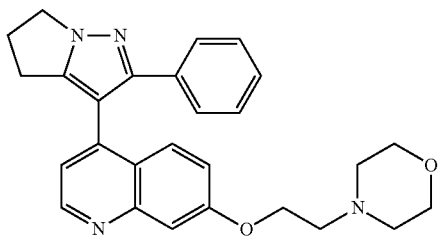 [SMILES: c1ccc(-c2nn3c(c2-c2ccnc4cc(OCCN5CCOCC5)ccc24)CCC3)cc1]

14. Polymorphs, solvates or hydrates of 2-(5-benzo[1,3]dioxol-5-yl-2-tert-butyl-3H-imidazol-4-yl)-6-methylpyridine hydrochloride (also known as SB-505124)
15. Polymorphs, solvates or hydrates of SD-093
16. Polymorphs, solvates or hydrates of 2-(5-Chloro-2-fluorophenyl)pteridin-4-yl]pyridin-4-yl-amine (also known as SD-208)
17. 6-(2-tert-butyl-5-(6-methylpyridin-2-yl)-1H-imidazol-4-yl)quinoxaline (also known as SB2525334) and polymorphs, solvates, and hydrates thereof
18. 4-(6-(4-(piperazin-1-yl)phenyl)pyrazolo[1,5-a]pyrimidin-3-yl)quinoline (also known as LDN 193189) and polymorphs, solvates, and hydrates thereof.
19. Polymorphs, solvates or hydrates of Ki 26894 as described by Ehata et al., Cancer Sci. 2007; 98:127-33.
20. Polymorphs, solvates or hydrates of 3-((5-(6-methylpyridin-2-yl)-4-(quioxalin-6-yl)-1H-imidazol-2-yl)methyl)benzamide (also known as IN-1130).
21. Polymorphs, solvates or hydrates of the TGF-β receptor type I kinase inhibitors as described in DaCosta Bayfield, (Mol. Pharmacol., 2004, 65:744-52), Laping, (Curr. Opin. Pharmacol., 2003, 3:204-8) and Laping (Mol. Pharmacol., 2002, 62:58-64)
22. Disitertide as described by Santiago et al. (J. Invest. Dermatol. 125, 450-455 (2005)
23. Lerdelimumab as described by Mead, A. L., et al., Invest. Ophthalmol. Vis. Sci. 44, 3394-3401 (2003) or any antigen-binding fragment thereof.
24. Metelimumab as described by Denton, C. P. Arthritis Rheum. 56, 323-333 (2007) or any antigen-binding fragment thereof.
25. Fresolimumab as described by Trachtman, H. et al. Kidney Int. 79, 1236-1243 (2011) or any antigen-binding fragment thereof.
26. LY2382770 or any antigen-binding fragment thereof
27. Polymorphs, solvates or hydrates of SM16

TABLE 1-continued

TGFbeta inhibitors.

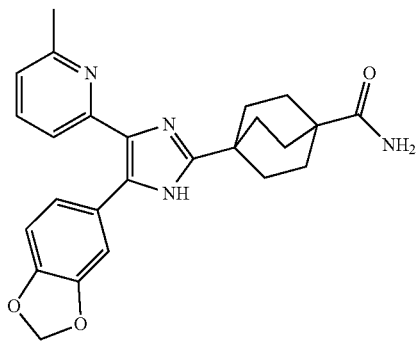

SM16 (Biogen Idec)

28 STC-100 as described by Allison, M. Nature Biotech. 30, 375-376 (2012) or any antigen-binding fragment thereof.
29 Dominant negative TGFBR2-modified CTLs
30 Avotermin as described by Occleston, N. L. et al.. Wound Repair Regen. 19 (Suppl. 1), S38-S48 (2011).
31 Pirfenidone as described by Sheppard, D. Proc. Am. Thorac. Soc. 3, 413-417 (2006) and polymorphs, solvates, and hydrates thereof.
32 Losartan as described by Holm, T. M. et al. Science 332, 358-361 (2011) and polymorphs, solvates, and hydrates thereof.
33 IMC-TR1 as described by Zhong, Z. et al. Clin. Cancer Res. 16, 1191-1205 (2010) or any antigen-binding fragment thereof.
34 AP11014 as described by Schlingensiepen, K. H. et al. J. Clin. Oncol. 22, Abstract 3132 (2004)
35 P17 as described by Llopiz, D. et al. Int. J. Cancer 125, 2614-2623, (2009).
36 LSKL as described by Lu, A., et al., Am. J. Pathol. 178, 2573-2586 (2011) and polymorphs, solvates, and hydrates thereof.
37 SR2F as described by J. Clin. Invest. 109, 1607-1615, (2002).
38 Fusion proteins comprising the TβR2 and Fc
39 4-(4-(3-(pyridin-2-yl)-1H-pyrazol-4-yl)pyridin-2-yl)-N-(tetrahydro-2H-pyran-4-yl)benzamide (also known as GW788388 and polymorphs, solvates, and hydrates thereof
40 GB1201 (50, 102, 103) as described by Yao, E. H. et al. Cardiovasc. Res. 81, 797-804 (2009) and polymorphs, solvates, and hydrates thereof
41 GB1203 as described by Yao, El H. et al. Cardiovasc. Res. 81, 797-804 (2009) and polymorphs, solvates, and hydrates thereof.
42 Compounds having the structure

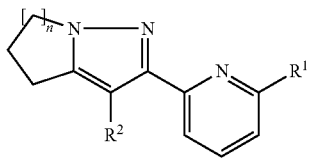

wherein n is 1-2
R1 is hydrogen or C1-C4 alkyl
R2 is selected from the group consisting of 1-H-pyrrolo[2,3-b], 1-H-pyrrolo[2,3c]pyridine, 1-H-pyrazolo[3,4-b]pyridine and 7-H-pyrrolo[2,3-d]pyrimidine all of which may be optionally substituted with C1-C4 alkyl or phenyl
and polymorphs, solvates, and hydrates thereof
as well as the compounds defined by the following structural formulae:

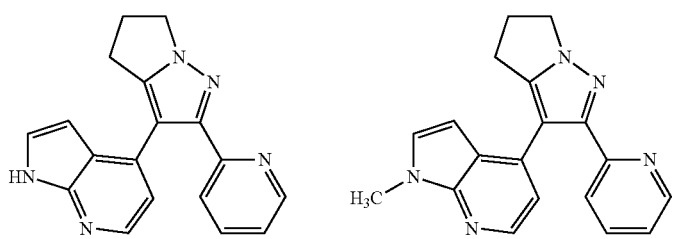 [SMILES: c1ccc(-c2nn3c(c2-c2ccnc4[nH]ccc24)CCC3)nc1 ; Cn1ccc2c(-c3c(-c4ccccn4)nn4c3CCC4)ccnc21]

TABLE 1-continued
TGFbeta inhibitors.
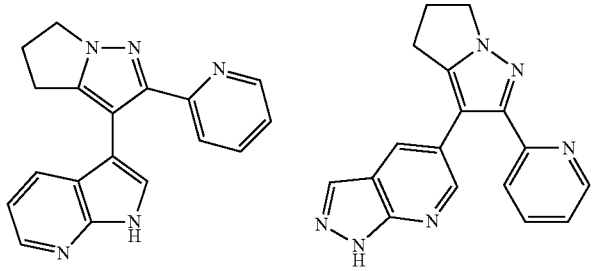 [SMILES: c1ccc(-c2nn3c(c2-c2c[nH]c4ncccc24)CCC3)nc1 ; c1ccc(-c2nn3c(c2-c2cnc4[nH]ncc4c2)CCC3)nc1]
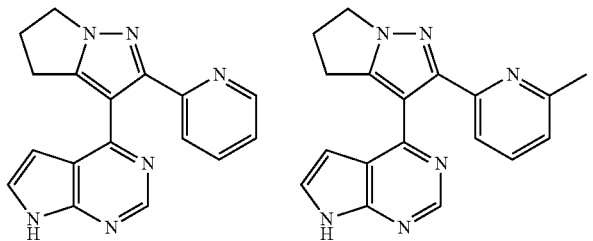 [SMILES: c1ccc(-c2nn3c(c2-c2ncnc4[nH]ccc24)CCC3)nc1 ; Cc1cccc(-c2nn3c(c2-c2ncnc4[nH]ccc24)CCC3)n1]
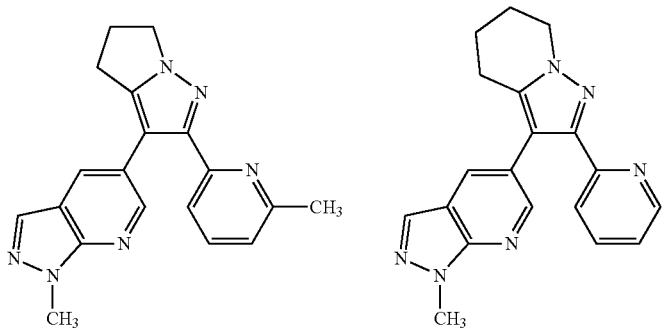 [SMILES: Cc1cccc(-c2nn3c(c2-c2cnc4c(cnn4C)c2)CCC3)n1 ; Cn1ncc2cc(-c3c(-c4ccccn4)nn4c3CCCC4)cnc21]
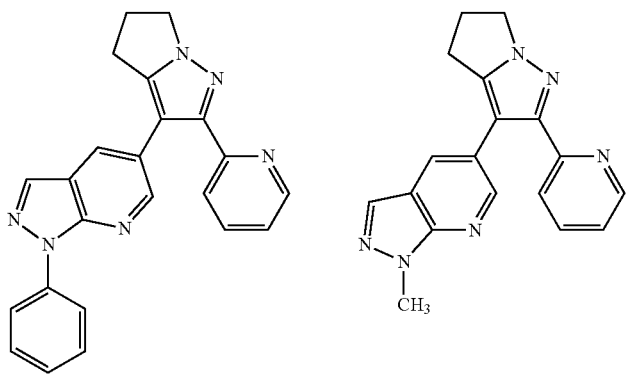 [SMILES: c1ccc(-n2ncc3cc(-c4c(-c5ccccn5)nn5c4CCC5)cnc32)cc1 ; Cn1ncc2cc(-c3c(-c4ccccn4)nn4c3CCC4)cnc21]
and polymorphs, solvates, and hydrates thereof.

TABLE 1-continued

TGFbeta inhibitors.

43 Compounds having the general structure

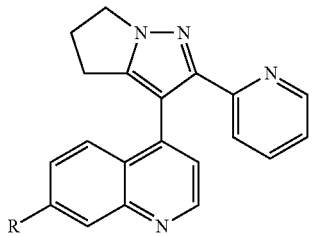

1: R = H
1a: R = NHCOCH$_2$N(CH$_3$)$_2$
1b: R = NH$_2$

Wherein R is H, NHCOCH$_2$N(CH$_3$)$_2$ or NH$_2$ and polymorphs, solvates, and hydrates thereof.

44 Compounds having the general structure

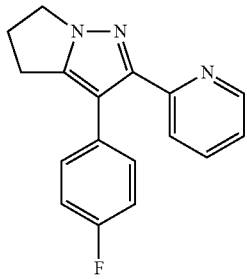 [SMILES: Fc1ccc(-c2c(-c3ccccn3)nn3c2CCC3)cc1]

and polymorphs, solvates, and hydrates thereof.

45 Compounds having the general structure

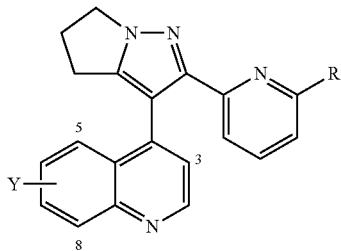

wherein Y is 7-OMe and R is H or
Y is 2-Cl and R is H or
Y is 6,8-(OMe)$_2$ and R is Me or
Y is 8-F and R is Me or
Y is 6-Br and R is Me or
Y is 6-OCF$_3$ and R is Me
and polymorphs, solvates, and hydrates thereof.

The term "polymorph", as used herein, refers to a particular crystalline state of a substance, having particular physical properties described by X-ray diffraction patterns, IR spectra, phase transition point, and the like. The different polymorphs may result from differences in crystal packing (packing polymorphism) or differences in packing between different conformers of the same molecule (conformational polymorphism).

In a preferred embodiment, the TGF-β inhibitor is a crystalline LY2157299 monohydrate characterized by the X-ray powder diffraction pattern (Cu radiation, λ=1.54056 Å) comprising a peak at 9.05 and one or more peaks selected from the group comprising 11.02, 11.95, and 14.84 (2θ+/−0.1°).

In a preferred embodiment, the TGF-β inhibitor is a crystalline LY2157299 monohydrate further characterized by the X-ray powder diffraction pattern (Cu radiation, λ=1.54056 Å) comprising a peak at 9.05 (2θ+/−0.1°).

In another preferred embodiment, the TGF-β inhibitor is a crystalline LY2157299 monohydrate further characterized by the solid state 13C nuclear magnetic resonance having a chemical shift (ppm) of 108.8, 115.6, 122.6, and 171.0 (+/−0.2) ppm.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces. When the solvent is water, the term "hydrate" is used instead of solvate.

The present invention further provides antibodies and antibody fragments that specifically bind with such polypeptides and neutralize the signaling activity of TGF-β. Exemplary neutralizing antibodies include polyclonal antibodies, murine monoclonal antibodies, humanized antibodies derived from murine monoclonal antibodies, and human monoclonal antibodies. Illustrative antibody fragments include F(ab')2, F(ab)2, Fab', Fab, Fv, scFv, and minimal recognition units.

The isolated exosome population forming part of the compositions of the invention is characterized by one or more of the following features:
  at least 20% of the exosomes have an average molecular weight of at least about 3 kDa,
  at least 20% of the exosomes have an average diameter between about 150 and about 300 nm,
  the exosomes from said population comprise TSP-1 and/or
  the exosomes show low TGF-β and/or low latent TGF-β levels In a particular embodiment, the MSCs are adipose tissue-derived stem cells (ASCs). In another embodiment, the MSCs derive from menstrual tissue. In another particular embodiment, the MSCs are human.

In a particular embodiment, at least 20%, at least 40%, at least 60%, at least 80%, at least 90%, at least 95% or at least 95% of the exosomes have an average molecular weight of at least about 3 kDa, for example at least about 3 kDa, for example, at least about 10, at least about 20, at least about 30, at least about 40, at least about 50, at least about 75, at least about 100 kDa.

In a particular embodiment, at least 20% of the exosomes have an average molecular weight of at least about 3 kDa. In another particular embodiment, at least 20% of the exosomes have an average molecular weight of at least about 10 kDa. In another particular embodiment, at least 20% of the exosomes have an average molecular weight of at least about 20 kDa. In another particular embodiment, at least 20% of the exosomes have an average molecular weight of at least about 30 kDa. In another particular embodiment, at least 20% of the exosomes have an average molecular weight of at least about 40 kDa. In another particular embodiment, at least 20% of the exosomes have an average molecular weight of at least about 50 kDa. In another particular embodiment, at least 20% of the exosomes have an average molecular weight of at least about 75 kDa. In another particular embodiment, at least 20% of the exosomes have an average molecular weight of at least about 100 kDa.

In a particular embodiment, at least 40% of the exosomes have an average molecular weight of at least about 3 kDa. In another particular embodiment, at least 40% of the exosomes have an average molecular weight of at least about 10 kDa. In another particular embodiment, at least 40% of the exosomes have an average molecular weight of at least about 20 kDa. In another particular embodiment, at least 40% of the exosomes have an average molecular weight of at least about 30 kDa. In another particular embodiment, at least 40% of the exosomes have an average molecular weight of at least about 40 kDa. In another particular embodiment, at least 40% of the exosomes have an average molecular weight of at least about 50 kDa. In another particular embodiment, at least 40% of the exosomes have an average molecular weight of at least about 75 kDa. In another particular embodiment, at least 40% of the exosomes have an average molecular weight of at least about 100 kDa.

In a particular embodiment, at least 60% of the exosomes have an average molecular weight of at least about 3 kDa. In another particular embodiment, at least 60% of the exosomes have an average molecular weight of at least about 10 kDa. In another particular embodiment, at least 60% of the exosomes have an average molecular weight of at least about 20 kDa. In another particular embodiment, at least 60% of the exosomes have an average molecular weight of at least about 30 kDa. In another particular embodiment, at least 60% of the exosomes have an average molecular weight of at least about 40 kDa. In another particular embodiment, at least 60% of the exosomes have an average molecular weight of at least about 50 kDa. In another particular embodiment, at least 60% of the exosomes have an average molecular weight of at least about 75 kDa. In another particular embodiment, at least 60% of the exosomes have an average molecular weight of at least about 100 kDa.

In a particular embodiment, at least 80% of the exosomes have an average molecular weight of at least about 3 kDa. In another particular embodiment, at least 80% of the exosomes have an average molecular weight of at least about 10 kDa. In another particular embodiment, at least 80% of the exosomes have an average molecular weight of at least about 20 kDa. In another particular embodiment, at least 80% of the exosomes have an average molecular weight of at least about 30 kDa. In another particular embodiment, at least 80% of the exosomes have an average molecular weight of at least about 40 kDa. In another particular embodiment, at least 80% of the exosomes have an average molecular weight of at least about 50 kDa. In another particular embodiment, at least 80% of the exosomes have an average molecular weight of at least about 75 kDa. In another particular embodiment, at least 80% of the exosomes have an average molecular weight of at least about 100 kDa.

In a particular embodiment, at least 90% of the exosomes have an average molecular weight of at least about 3 kDa. In another particular embodiment, at least 90% of the exosomes have an average molecular weight of at least about 10 kDa. In another particular embodiment, at least 90% of the exosomes have an average molecular weight of at least about 20 kDa. In another particular embodiment, at least 90% of the exosomes have an average molecular weight of at least about 30 kDa. In another particular embodiment, at least 90% of the exosomes have an average molecular weight of at least about 40 kDa. In another particular embodiment, at least 90% of the exosomes have an average molecular weight of at least about 50 kDa. In another particular embodiment, at least 60% of the exosomes have an average molecular weight of at least about 75 kDa. In another particular embodiment, at least 90% of the exosomes have an average molecular weight of at least about 100 kDa.

In a particular embodiment, at least 95% of the exosomes have an average molecular weight of at least about 3 kDa. In another particular embodiment, at least 95% of the exosomes have an average molecular weight of at least about 10 kDa. In another particular embodiment, at least 95% of the exosomes have an average molecular weight of at least about 20 kDa. In another particular embodiment, at least 95% of the exosomes have an average molecular weight of at least about 30 kDa. In another particular embodiment, at least 95% of the exosomes have an average molecular weight of at least about 40 kDa. In another particular embodiment, at least 95% of the exosomes have an average molecular weight of at least about 50 kDa. In another particular embodiment, at least 60% of the exosomes have an average molecular weight of at least about 75 kDa. In another particular embodiment, at least 95% of the exosomes have an average molecular weight of at least about 100 kDa.

In a particular embodiment, at least 99% of the exosomes have an average molecular weight of at least about 3 kDa. In another particular embodiment, at least 99% of the exosomes have an average molecular weight of at least about 10 kDa. In another particular embodiment, at least 99% of the exosomes have an average molecular weight of at least about 20 kDa. In another particular embodiment, at least 99% of the exosomes have an average molecular weight of at least about 30 kDa. In another particular embodiment, at least 99% of the exosomes have an average molecular weight of at least about 40 kDa. In another particular embodiment, at least 99% of the exosomes have an average molecular weight of at least about 50 kDa. In another particular embodiment, at least 99% of the exosomes have an average molecular weight of at least about 75 kDa. In another particular embodiment, at least 99% of the exosomes have an average molecular weight of at least about 100 kDa.

In a particular embodiment, at least 20%, at least 40%, at least 60%, at least 80%, at least 90%, at least 95% or at least 95% of the exosomes have an average diameter between about 150 and about 300 nm, more particularly between about 223 and about 300 nm, even more particularly between about 150 and about 193.5 nm.

In a particular embodiment, at least 20% of the exosomes have an average diameter between about 150 and about 300 nm. In another particular embodiment, at least 20% of the exosomes have an average diameter between about 223 and about 300 nm. In another particular embodiment, at least 20% of the exosomes have an average diameter between about 150 and about 193.5 nm.

In a particular embodiment, at least 40% of the exosomes have an average diameter between about 150 and about 300 nm. In another particular embodiment, at least 40% of the exosomes have an average diameter between about 223 and about 300 nm. In another particular embodiment, at least 40% of the exosomes have an average diameter between about 150 and about 193.5 nm.

In a particular embodiment, at least 60% of the exosomes have an average diameter between about 150 and about 300 nm. In another particular embodiment, at least 60% of the exosomes have an average diameter between about 223 and about 300 nm. In another particular embodiment, at least 60% of the exosomes have an average diameter between about 150 and about 193.5 nm.

In a particular embodiment, at least 80% of the exosomes have an average diameter between about 150 and about 300 nm. In another particular embodiment, at least 80% of the exosomes have an average diameter between about 223 and about 300 nm. In another particular embodiment, at least 80% of the exosomes have an average diameter between about 150 and about 193.5 nm.

In a particular embodiment, at least 90% of the exosomes have an average diameter between about 150 and about 300 nm. In another particular embodiment, at least 90% of the exosomes have an average diameter between about 223 and about 300 nm. In another particular embodiment, at least 90% of the exosomes have an average diameter between about 150 and about 193.5 nm.

In a particular embodiment, at least 95% of the exosomes have an average diameter between about 150 and about 300 nm. In another particular embodiment, at least 95% of the exosomes have an average diameter between about 223 and about 300 nm. In another particular embodiment, at least 95% of the exosomes have an average diameter between about 150 and about 193.5 nm.

In a particular embodiment, at least 20% of the exosomes of the composition according to the invention have an average molecular weight of at least about 3 kDa and at least 20% of the exosomes of the population have an average diameter between about 150 and about 300 nm.

In another particular embodiment, at least 20% of the exosomes of composition according to the invention have an average molecular weight of at least about 3 kDa and the exosomes of the population comprise TSP-1.

In another particular embodiment, at least 20% of the exosomes of composition according to the invention have an average diameter between about 150 and about 300 nm and comprises TSP-1.

In another particular embodiment, at least 20% of the exosomes of the composition according to the invention have an average molecular weight of at least about 3 kDa, at least 20% of the exosomes of the population have an average diameter between about 150 and about 300 nm and the exosomes of the population comprise TSP-1.

In a preferred embodiment, the TGF-β inhibitor is selected from the group comprising the inhibitors shown in Table 1.

In another embodiment, the isolated exosome population forming part of the compositions of the invention is characterized in that it has been obtained by a method comprising the steps of
 a) filtering a cell-free MSC-conditioned medium using a 3 kDa cut-off membrane and recovering the retentate, or
 b) centrifuging a cell-free MSC-conditioned medium at a speed sufficient to precipitate exosomes and recovering the pellet.

In a particular embodiment, the MSCs are adipose tissue-derived stem cells (ASCs). In a particular embodiment, the MSCs are MSCs derived from menstrual tissue. In another particular embodiment, the MSCs are human.

In a particular embodiment, the MSC-conditioned medium does not comprise any type of sera, including fetal bovine serum, bovine serum (BS), calf serum (CS), fetal calf serum (FCS), newborn calf serum (NCS), goat serum (GS), horse serum (HS), porcine serum, sheep serum, rabbit serum, rat serum (RS). In another particular embodiment, the MSC-conditioned medium comprises insulin-transferrin-selenium. In a more particular embodiment, the MSC-conditioned medium is DMEM containing 1% insulin-transferrin-selenium. In a particular embodiment, the MSC-conditioned medium has been contacted with the MSC culture for at least 1 hour, at least 2 hours, at least 6 hours, at least 12 hours, at least 24 hours, at least 2 days, at least 3 days, at least 4 days, at least 5 days or more. In a more particular embodiment, the MSC-conditioned medium has been contacted with the MSCs for 3 or 4 days. The cell-free MSC-conditioned medium can be obtained by any method known by the skilled person that allows recovering a culture medium without the cells. For example, the medium can be collected from a monolayer culture of MSCs.

In a particular embodiment, the cell-free MSC conditioned medium is obtained by collecting the medium from MSCs culture, centrifuging said medium in order to remove cells and debris and collecting the supernatant. In a more particular embodiment, cells and debris are removed by subjecting the medium to two successive centrifugations at 1000×g and 5000×g respectively. In an even more particular embodiment, these centrifugations are performed at 4° C. In a still more particular embodiment, the first centrifugation lasts about 10 minutes and the second centrifugation lasts about 20 minutes.

In a particular embodiment, the speed sufficient to precipitate exosomes is between 100,000 g and 1,000,000 g, and therefore, the centrifugation is an ultracentrifugation. In a more particular embodiment, the centrifugation is performed at 100000×g. In a particular embodiment, the centrifugation lasts between 30 minutes and 12 hours. In a more particular embodiment, the centrifugation lasts between 2 hour and 10 hours. In an even more particular embodiment the centrifugation lasts about 6 hours.

Pharmaceutical Composition of the Invention

In a sixth aspect, the invention relates to a pharmaceutical composition, hereinafter pharmaceutical composition of the invention, comprising an exosome according to the first aspect of the invention, an isolated exosome population according to the second or fourth aspects or a composition according to the fifth aspect of the invention.

The term "pharmaceutical composition", as used herein, refers to a composition comprising a therapeutically effective amount of the agent according to the present invention, i.e., the exosome of the first aspect or the isolated exosome population of the second or fourth aspect, and at least one pharmaceutically acceptable excipient.

The terms "pharmaceutically acceptable excipient", or "pharmaceutically acceptable carrier," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation.

The person skilled in the art will appreciate that the nature of the excipient in the pharmaceutical composition of the invention will depend to a great extent on the administration route. In the case of the pharmaceutical compositions formulated for their oral (or topical) use, a pharmaceutical composition according to the invention normally contains the pharmaceutical composition of the invention mixed with one or more pharmaceutically acceptable excipients. These excipients can be, for example, inert fillers or diluents, such as sucrose, sorbitol, sugar, mannitol, microcrystalline cellulose, starches, including potato starch, calcium carbonate, sodium chloride, lactose, calcium phosphate, calcium sulfate or sodium phosphate; crumbling agents and disintegrants, for example cellulose derivatives, including microcrystalline cellulose, starches, including potato starch, sodium croscarmellose, alginates or alginic acid and chitosans; binding agents, for example sucrose, glucose. sorbitol, acacia, alginic acid, sodium alginate, gelatin, starch, pregelatinized starch, microcrystalline cellulose, aluminum magnesium silicate, sodium carboxymethylcellulose, methylcellulose, hydroxypropyl methylcellulose, ethylcellulose, polyvinylpyrrolidone, polyvinyl acetate or polyethylene glycol, and chitosans; lubricating agents, including glidants and antiadhesive agents, for example magnesium stearate, zinc stearate, stearic acid, silicas, hydrogenated vegetable oils or talc.

In a particular preferred embodiment, the pharmaceutical compositions of the invention is formulated for administration via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir.

Pharmaceutical compositions according to the invention can be prepared, for instance, as injectables such as liquid solutions, suspensions, and emulsions.

Method of Treating an Immune-Mediated Inflammatory Disease of the Invention

In a seventh aspect, the invention relates to a method of treating an immune-mediated inflammatory disease in a subject suffering from said disease, which comprises administering to said subject a therapeutically effective amount of the exosome according to the first aspect, or the isolated exosome population of the second or fourth aspect, the composition according to the fifth aspect the pharmaceutical composition of the sixth aspect. The invention also relates to the exosome according to the first aspect, the isolated exosome population of the second or fourth aspects, the composition according to the fifth aspect or the pharmaceutical composition of the sixth aspect for use in a method of treating an immune-mediated inflammatory disease. The invention also relates to the use of the exosome according to the first aspect, of the isolated exosome population of the second or fourth aspects, of the composition according to the fifth aspect or of the pharmaceutical composition of the sixth aspect for the preparation of a medicament for the treatment of an immune-mediated inflammatory disease.

The term "method of treating", as used herein, means the administration of the exosome of the first aspect, or the isolated exosome population of the second or the fourth aspect, or the pharmaceutical composition of the fifth aspect, to preserve health in a subject suffering from an immune-mediated inflammatory disease, including preventing, ameliorating or eliminating one or more symptoms associated with said disease.

The term "immune-mediated inflammatory disease" or "IMID", as used herein, refers to any of a group of conditions or diseases that lack a definitive etiology, but which are characterized by common inflammatory pathways leading to inflammation, and which may result from, or be triggered by, a deregulation of the normal immune response. Because inflammation mediates and is the primary driver of many medical and autoimmune disorders, within the context of the present invention, the term immune-mediated inflammatory disease is also meant to encompass autoimmune disorders and inflammatory diseases.

The term "autoimmune disorder", as used herein, refers to a condition in a subject characterised by cellular, tissue and/or organ injury caused by an immunological reaction of the subject to its own cells, tissues and/or organs. Illustrative, non-limiting examples of autoimmune diseases which can be treated with the methods or pharmaceutical compositions of the invention include alopecia areata, rheumatoid arthritis (RA), ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, anti-glomerular gasement membrane disease, antiphospholipid syndrome, autoimmune diseases of the nervous system, familial mediterranean fever, Lambert-Eaton myasthenic syndrome, sympathetic ophthalmia, polyendocrinopathies, psoriasis, etc.

The term "inflammatory disease", as used herein, refers to a condition in a subject characterised by inflammation, e.g. chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, Crohn's disease, ulcerative colitis, allergic disorders, septic shock, pulmonary fibrosis (e.g; idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g. restenosis after angioplasty), undifferentiated spondyloarthropathy, undifferentiated arthropathy, arthritis, inflammatory osteolysis, chronic hepatitis, chronic inflammation resulting from chronic viral or bacterial infections, and acute inflammation, such as sepsis.

In a particular embodiment, the immune-mediated inflammatory disease is selected from the group consisting of rheumatoid arthritis (RA), Inflammatory Bowel Disease (IBD), and Crohn's disease.

The term "rheumatoid arthritis" or "RA", as used herein, refers to a systemic autoimmune inflammatory pathology, characterized by causing persistent synovitis of the joints, causing their progressive destruction, generating different degrees of deformity and functional disability. The process starts with the intervention of humoral and cell factors, particularly CD4 T-cells, which generate inflammation mediating molecules, attract and activate peripheral blood cells, causing proliferation and activation of the synoviocytes, invading and destroying joint cartilage, subchondral bone, tendons and ligaments.

The term "inflammatory bowel disease" or "IBD", refers to a group of inflammatory conditions of the colon and small intestine, which include ulcerative colitis, collagenous colitis, lymphocytic colitis, ischaemic colitis, diversion colitis, Behcet's disease, and indeterminate colitis.

The term "Crohn's disease", as used herein, refers to a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss, but may also cause complications outside the gastrointestinal tract such as anaemia, skin rashes, arthritis, inflammation of the eye, tiredness, and lack of concentration. Crohn's disease is caused by interactions between environmental, immunological and bacterial factors in genetically susceptible individuals. This results in a chronic inflammatory disorder, in which the body's immune system attacks the gastrointestinal tract. While Crohn's is an immune related disease, it does not appear to be an autoimmune disease (in that the immune system is not being triggered by the body itself).

The term "subject" has been previously defined. The term "subject suffering from said disease" means a subject that has been diagnosed with the disease.

The MSCs from which the exosomes derived can be autologous, allogeneic or xenogeneic. As used herein, the term "autologous" means that the donor of the MSCs and the recipient of the exosome (or isolated exosome population) derived from said MSCs are the same subject. The term "allogeneic" means that the donor of the MSCs and the recipient of the exosome (or isolated exosome population) derived from said MSCs are different subjects. The term "xenogeneic" means that the donor of the MSCs and the recipient of the exosome (or isolated exosome population) derived from said MSCs are subjects of different species. In a particular embodiment, the MSC's from which the exosomes derived are allogeneic.

In a particular embodiment, the exosome or the isolated exosome population is administered systemically or locally. The term "systemically" means that the exosome, isolated exosome population or pharmaceutical composition of the invention may be administered to a subject in a non-localized manner. The systemic administration of the exosome, isolated exosome population or pharmaceutical composition of the invention may reach several organs or tissues throughout the body of the subject or may reach specific organs or tissues of the subject. The term "locally administered", as used herein, means that the exosome, isolated exosome population or pharmaceutical composition of the invention may be administered to the subject at or near a specific site. In a more particular embodiment, the exosome or the isolated exosome population is administered via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir.

In a particular embodiment, the exosome or the isolated exosome population is administered in conjunction with at least one additional therapeutic agent. The term "therapeutic agent", as used herein, refers to an agent useful in the treatment of a disease. In a particular embodiment, the additional therapeutic agent is a known drug for the treatment of said immune-mediated inflammatory disease, like for example but not limited to corticosteroids or non-steroidal anti-inflammatory compounds.

The expression "administered in conjunction" means that the exosome, isolated exosome population or pharmaceutical composition of the invention can be administered jointly or separately, simultaneously, at the same time or sequentially with the additional therapeutic agent, for example a therapeutic useful in the treatment of a disease associated with inflammation, in any order. For example, the administration of the exosome, isolated exosome population or pharmaceutical composition of the invention can be done first, followed by the administration of one or more additional therapeutic agents; or the administration of the exosome, isolated exosome population or pharmaceutical composition of the invention can be done last, preceded by the administration of one or more additional therapeutic agents; or the administration of the exosome, isolated exosome population or pharmaceutical composition of the invention can be done at the same time as the administration of one or more additional therapeutic agents.

In one embodiment, the patient which is to be treated using the methods according to the present invention is being treated or has been treated with a therapy comprising a TGF-β inhibitor.

The invention is defined by way of the following examples, which are merely illustrative and in no way limitative of the scope of the invention.

EXAMPLES

Example 1

Materials and Methods
Human Adipose Mesenchymal Stem Cells Isolation and Expansion The human adipose mesenchymal stem cells (hASCs) were isolated from lipoaspirates obtained from human adipose tissue from healthy adult donors. Lipoaspirates were washed with PBS, and digested with collagenase type I in PBS. The digested sample was washed with 10% of fetal bovine serum (FBS), treated with ammonium chloride 160 mM, suspended in culture medium (DMEM containing 10% FBS), and filtered through a 40 μm nylon mesh. Cells were seeded onto tissue culture flasks and expanded at 37° C. and 5% $CO_2$, changing the culture medium every 7 days. Cells were passed to a new culture flask when cultures reached 90% of confluence. In addition, hASCs were tested by flow cytometry using specific surface markers being negative for CD14, CD31, CD34, CD45 and positive for CD29, CD59, CD90, and CD105 (data not shown). Cell lines from two healthy donors were used in the study. The biological samples were obtained after informed consent under the auspices of the appropriate Research and Ethics Committees.

Isolation and Purification of Exosomes from hASCs

An enriched fraction of exosomes from hASCs (exo-hASCs) was obtained from hASCs cultured in 175 $cm^2$ flasks. When cells reached a confluence of 80%, culture medium (DMEM containing 10% FBS) was replaced by exosome isolation medium (DMEM containing 1% insulin-transferrin-selenium). The hASCs supernatants were collected every 3-4 days. Exosomes were isolated from supernatants by two successive centrifugations at 1000×g (10 min) and 5000×g (20 min) at 4° C. to eliminate cells and debris, followed by an ultracentrifugation at 100,000×g for 6 h to precipitate exosomes. The pellets were resuspended in 250 μL of PBS and stored at −20° C. Prior to in vitro experiments, exosomes were quantified by Bradford assays and characterized by nanoparticle tracking analysis.

Characterization of Exo-hASCs

The concentration and size of purified exosomes were measured by nanoparticle tracking analysis (NanoSight Ltd, Amesbury, UK) that relates the rate of Brownian motion to particle size. Results were analyzed using the nanoparticle tracking analysis software package version 2.2. Triplicate samples were diluted 1:10 in sterile-filtered PBS and analyzed.

Bradford Assay

Exosome concentrations were indirectly measured by protein quantification in a Bradford assay. To quantify protein concentration, 20 μL of exosomes sample were incubated with 180 μL of Bradford reagent (Bio Rad Laboratories, Hercules, CA) at RT. Absorbance was read 5 min after at 595 nm, and protein concentration was extrapolated from a standard concentration curve of Bovine Serum Albumin.

Semicuantitative Identification of Proteins
Protein isolation:
  Protein Digestion using the method described by Bonzon-Kulichenko et al., Mol. Cell Proteomics 2011, 10(1):M110.003335. Briefly: 50 μg proteins were resuspended in 75 μl of a buffer (5% SDS, 10% glicerol, 25 mMTris-C1, 10 mM DTT y 0.01% azul de bromofenol a pH 6.8)
  Samples were separated by SDS-poliacrilamide gel. Proteins were visualized with Coomassie blue, were cutted and digested (37° C. with 60 ng/μl tripsin at ratio de 5:1 protein:tripsin (w/w) in 50 mM Ammonium bicarbonate pH 8.8 and 10% (v/v) acetonitrile and 0.01% (w/v) 5-ciclohexil-1-pentil-β-D maltoside.
Resulting peptides were analysed by LC-MS/MS, using a system Easy-nLC 1000 plus quadruple-Orbitrap hybrid mass spectrometer (Q-Exactive, Thermo Scientific, San Jose, CA).
Protein identification was performed using SEQUEST (Protein Discoverer 1.3.0.339, Thermo Scientific) and Swissprot (Uniprot release 2012-5) database.
SEQUEST results were validated as described in Navarro P et al. J Proteome Res. 2009, 8(4):1792-6.

Lymphocytes Isolation and Preservation

Peripheral blood lymphocytes (PBLs) from healthy donors were obtained by centrifugation over Histopaque-1077 (Sigma, St. Louis, MO, USA) and washed twice with PBS. The PBLs were frozen and stored in liquid nitrogen. For in vitro experiments, cell aliquots were thawed at 37° C., added to 10 mL of RPMI 1640 and centrifuged at 1500 rpm for 5 min to eliminate DMSO. Pellet was resuspended in RPMI 1640 supplemented with 10% of FBS.

In Vitro Stimulation of T Cells and Co-Culture with Exosomes

To determine the immunomodulatory effect of exo-hASCs on in vitro stimulated PBLs, $2\times10^5$ purified PBLs were seeded in a 96 wells plate (200 μl per well). To stimulate PBLs, a T cell activation/expansion kit (Miltenyi Biotec Inc, San Diego, CA, USA) was used, adding 5 μL of microbeads coated with anti-CD2/anti-CD3/anti-CD28 to each well. Finally, exosomes at different concentrations (4, 8, and 16 μg/$10^6$ PBLs) were added to wells. The PBLs were cultured for 6 days. Negative controls (non-stimulated PBLs) and positive controls (stimulated PBLs without exosomes) were used in all the experiments.

CFSE Proliferation Assay

The proliferative behavior of T cells was quantified by carboxyfluorescein succinimidyl ester (CFSE) dilution. The CFSE staining was performed before seeding, using the CFSE cell proliferation kit (Invitrogen, Eugene, OR) at a final concentration of 10 μM for 10 min at 37° C., followed by immediate quenching with culture medium. After 6 days, in vitro stimulated PBLs in the presence or absence of exo-hASCs were tested for CFSE dilution by flow cytometry.

Differentiation/Activation Markers Expression Analysis on In Vitro Stimulated PBLs For flow cytometric analysis of in vitro stimulated PBLs, the cells were collected from wells after 6 days by pipetting up and down. The cells were stained with fluorescence-labeled human mono-clonal antibodies against CD3 (SK7), CD4 (SK3), CD8 (SK1), CCR7 (3D12), CD45RA (L48) (BD Biosciences, San Jose, CA, USA). The markers expression analysis was performed as follows: $2\times10^5$ cells were incubated for 30 min at 4° C. with appropriate concentrations of monoclonal antibodies in the presence of PBS containing 2% FBS. The cells were washed and resuspended in PBS. The flow cytometric analysis was performed on a FAC-Scalibur cytometer (BD Biosciences, San Jose, CA, USA) after acquisition of $10^5$ events. Cells were primarily selected using for-ward and side scatter characteristics and fluorescence was analyzed using CellQuest software (BD Biosciences, San Jose, CA, USA). Isotype-matched negative control antibodies were used in all the experiments. The mean relative fluorescence intensity was calculated by dividing the mean fluorescent intensity (MFI) by the MFI of its negative control.

Intracellular Gamma-Interferon Assay

For IFN-γ assays, the PBLs were in vitro stimulated with the T cell activation/expansion kit (Miltenyi Biotec Inc, San Diego, CA, USA) for 6 days in the presence of exo-hASCs at 16 μg/$10^6$ PBLs. The PBLs were then incubated for 6 h with BD GolgiStop. PBLs were stained with PerCP-labeled anti-CD4 (SK3) and APC-labeled anti-CD8 (SK1), fixed and permeabilized using BD Cytofix/Cytoperm fixation/permeabilization kit. Finally, cells were stained with PE-labeled anti-IFN-γ antibody (all reagents from BD Biosciences, San Jose, CA, USA). Analysis by flow cytometry was performed by measuring the frequency of IFN-γ expression on gated CD3+CD4+ and CD3+CD8+ cells.

Statistical Analysis

Data were statistically analyzed using the Student's t-test for variables with parametric distribution. For the proliferation assay, an ANOVA with post hoc Bonferroni test was performed. The p-values ≤0.10 or ≤0.05 were considered statistically significant. All the statistical determinations were made using SPSS-21 software (SPSS, Chicago, IL, USA).

Results

Size Distribution and Concentration of Exo-hASCs

Figure 1B:
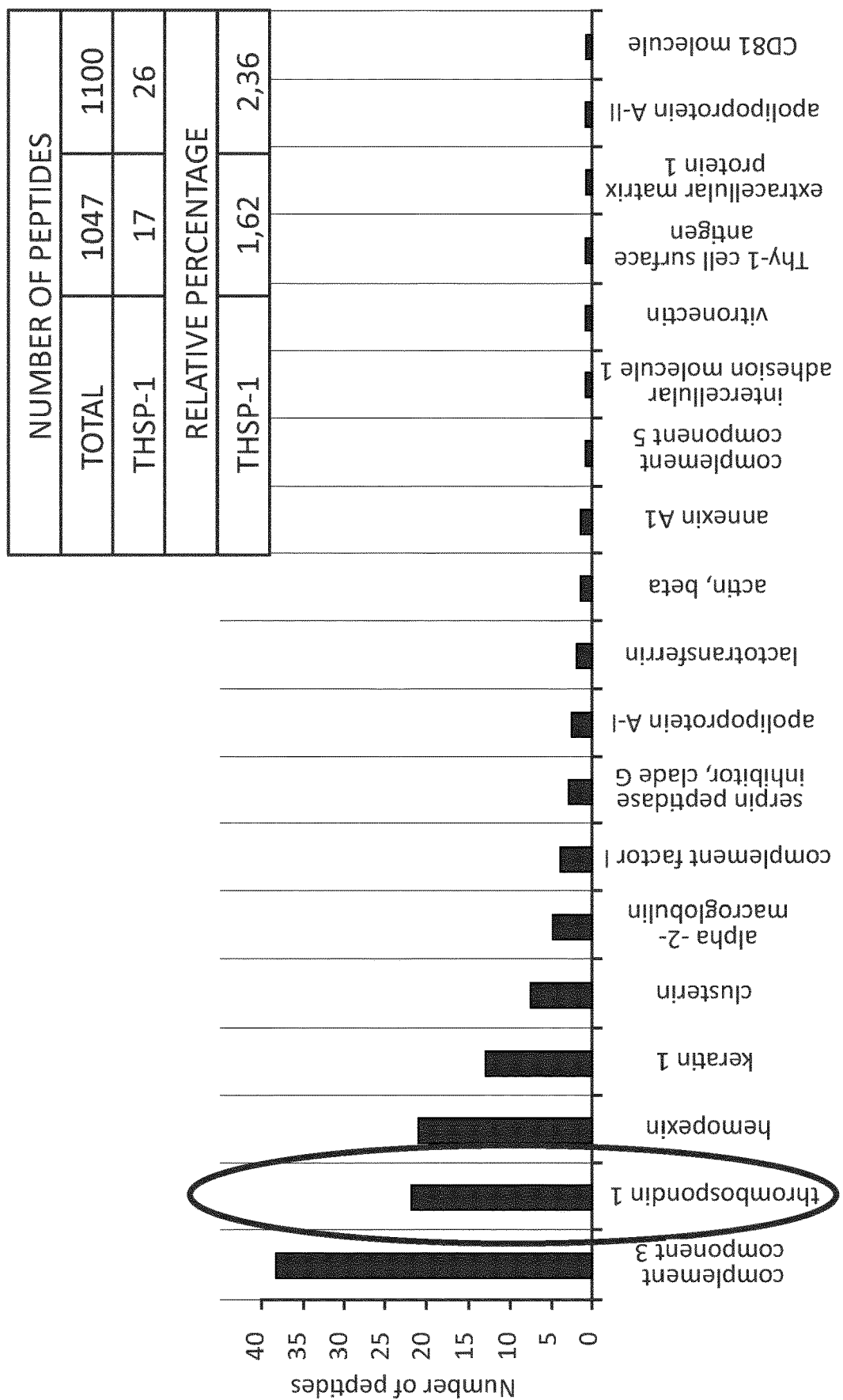

An enriched fraction of exosomes was collected from hASCs by ultracentrifugation. The protein concentration of exosomes was determined by Bradford assay. Three independently performed nanoparticle tracking analysis were performed for each exosome sample to quantify size distribution and particle concentration. Firstly, total protein concentration allowed exosome quantification for in vitro assays. Secondly, the nanoparticle tracking analysis allowed the characterization of the released vesicles. The size of isolated vesicles ranged from 223 to 300 nm and the mean size and standard deviation was 246.8±25.05 nm. Representative results of exo-hASCs are displayed as a frequency size distribution graph (FIG. 1A). The concentration of exosomes (n=6) was determined by nanoparticle tracking analysis and ranged between 8.4 and 9.7 ($\times10^9$) particles per milliliter and the mean concentration was 9.1±0.5 ($\times10^9$) particles per milliliter. Finally, the peptide content in the exosomes was analyzed by LC-MS/MS using an Easy-nLC 1000 system coupled to quadruple-Orbitrap hybrid mass spectrometer (Q-Exactive, Thermo Scientific, San Jose, CA). Protein identification was carried with SEQUEST (Protein Discoverer 1.3.0.339, Thermo Scientific) using the human SwissProt database. The TSP1 peptide was the second more abundant from a total of 110 identified proteins (FIG. 1B).

Figure 2:
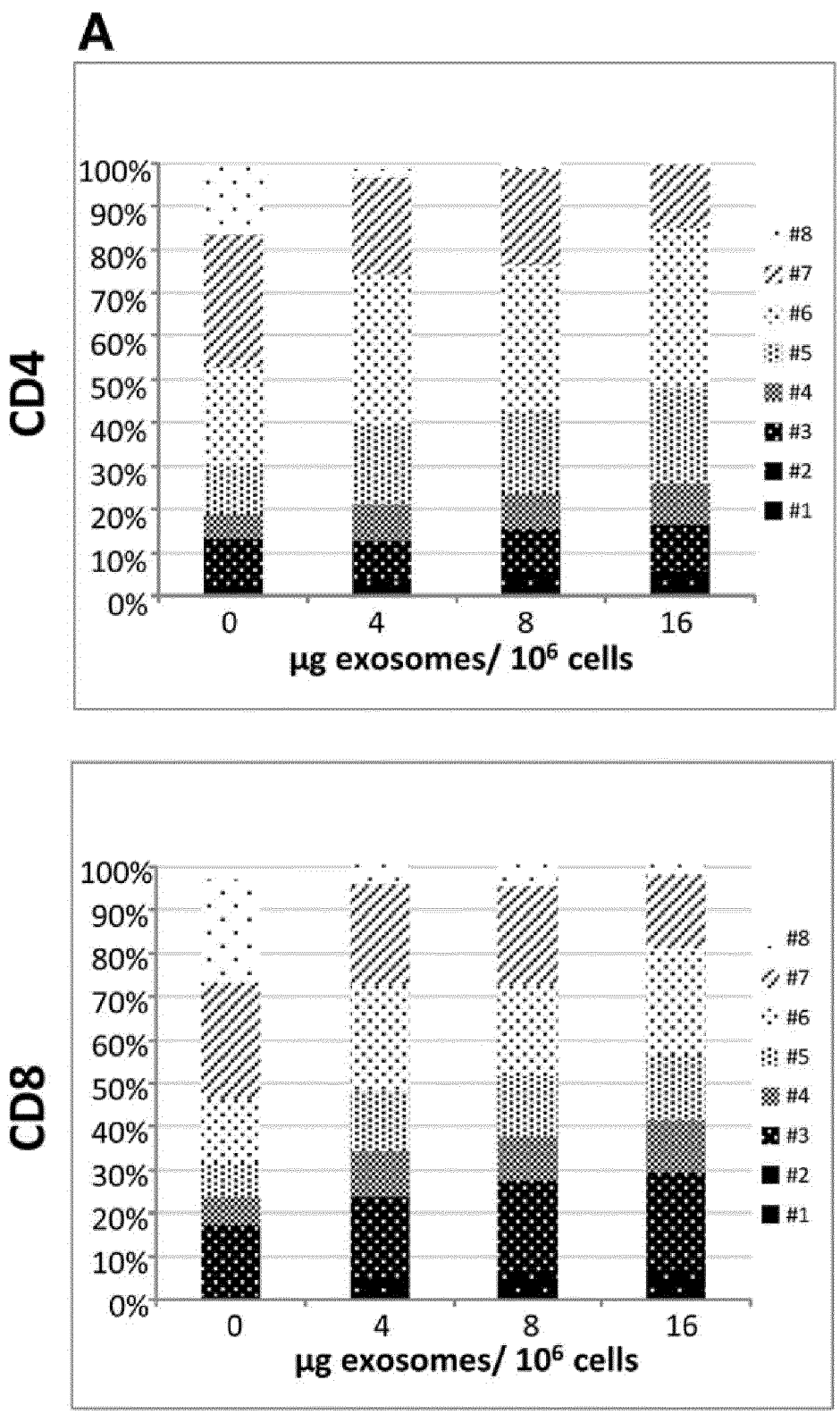
FIG. 2. The proliferative ability of in vitro stimulated PBLs is reduced by exo-hASCs. The PBLs were cultured either alone or co-cultured with different batches of exo-hASCs (nD8) at different concentrations (4, 8, and 16 mg of exosomes per million of PBLs). At day six, PBLs were collected and T-lymphocytes subsets were stained with anti-CD3, anti-CD4, and anti-CD8. Fluorescence profiles of CFSE-labeled cells allowed us to identify eight divisions. A detailed representation of CD4$^+$T cells and CD8$^+$T cells showing the percentage of the total population in each cell division cycle (indicated as #) is provided (A), as well as a representative histogram (B). The statistical comparison of lymphocyte subsets at different cell division cycles is also provided (C). Horizontal bars represent statistically significant differences between the groups (significant at p±0.05).
Figure 2:
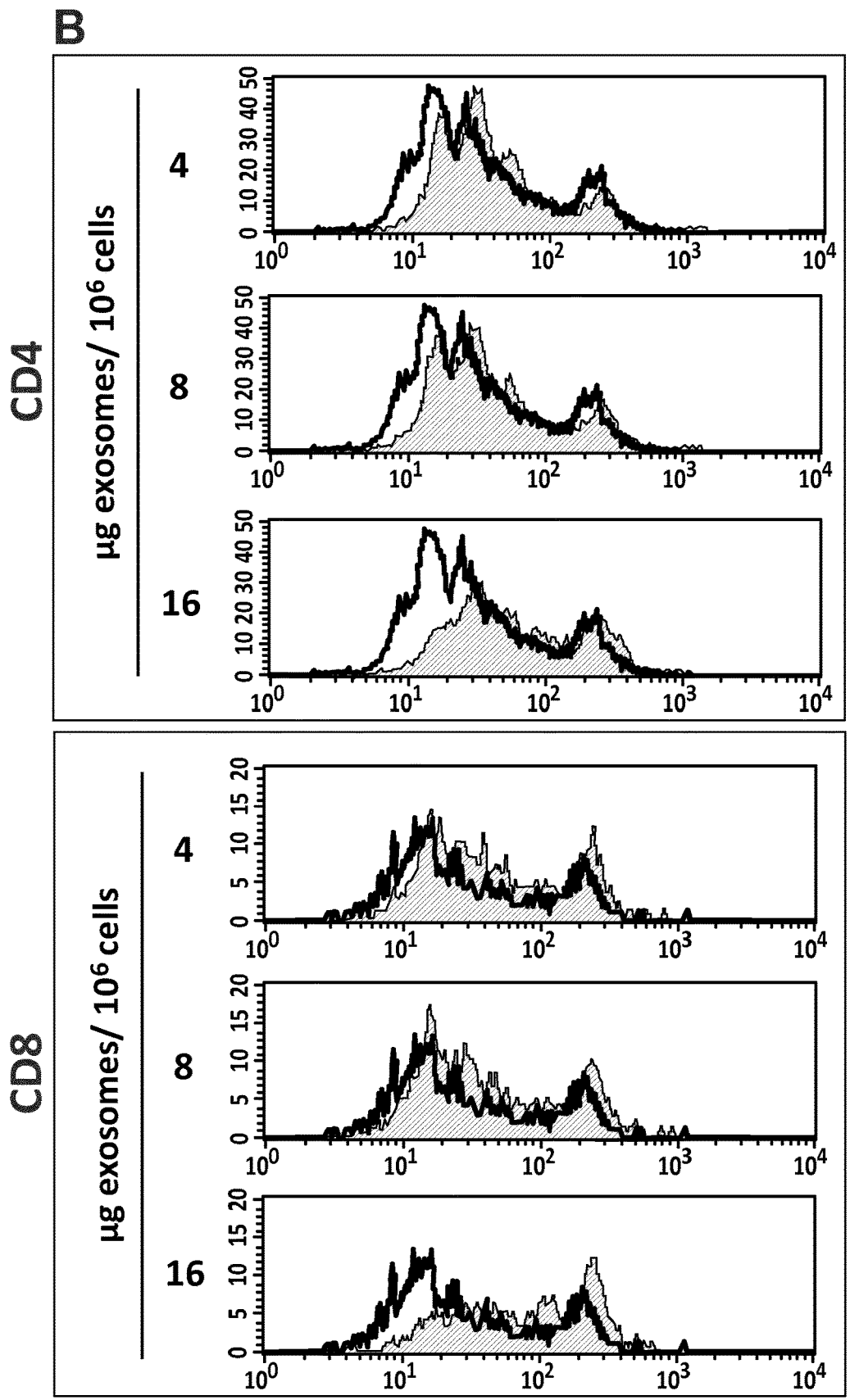
Figure 2:
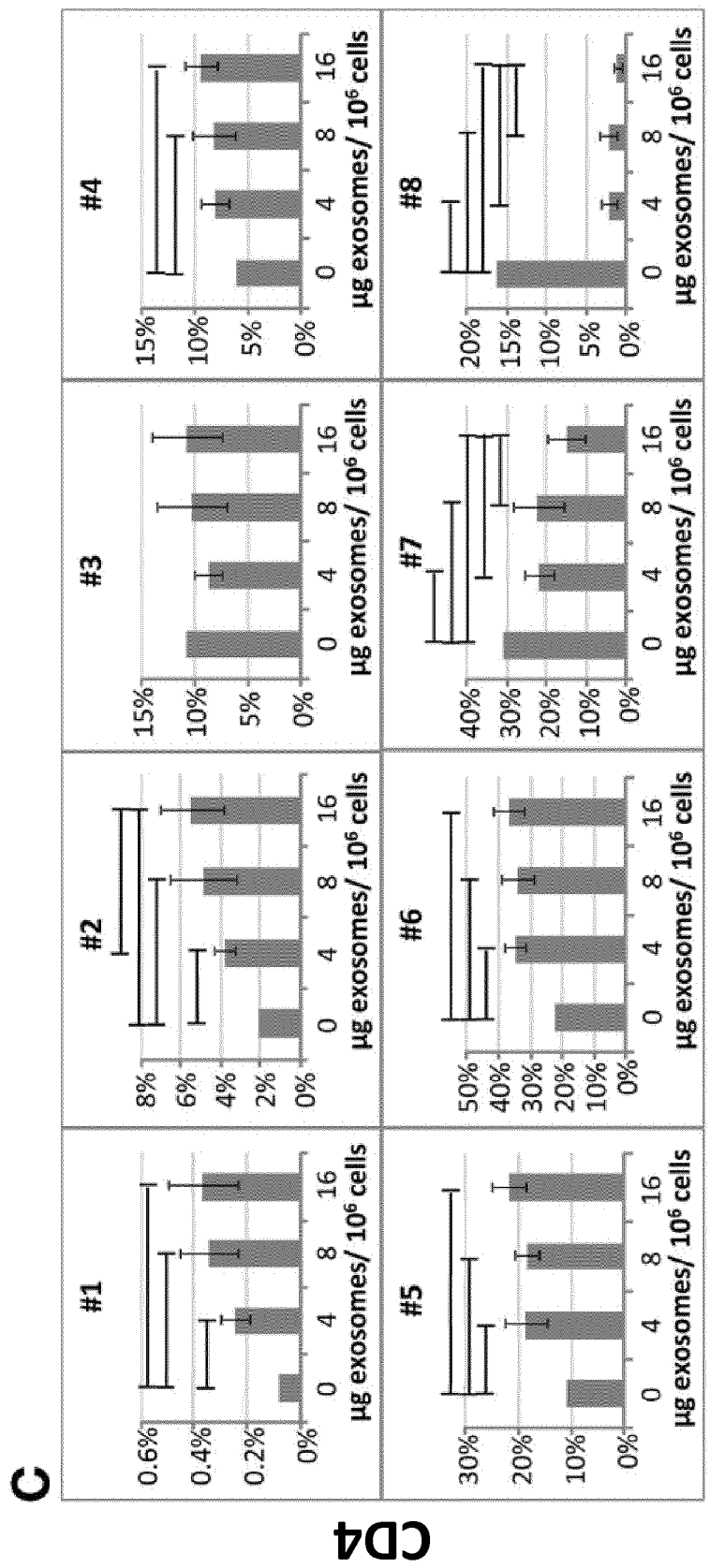
Figure 2:
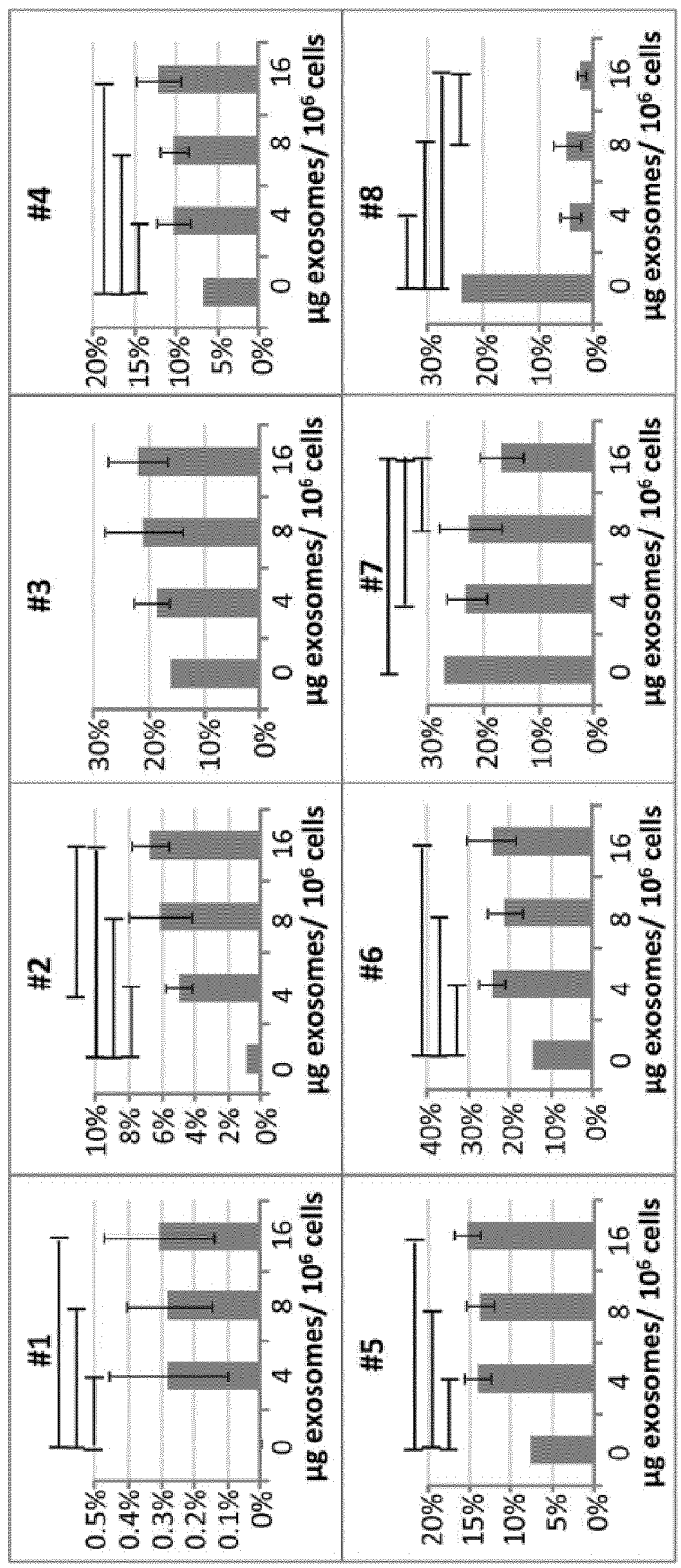

Proliferative Ability of the In Vitro Stimulated T Cells Co-Cultured in the Presence of Cells Co-Cultured in the Presence of Exo-hASCs In order to assess the biological activity of exo-hASCs, their effect over the proliferation rate of lymphocyte subsets was determined. For that, a total of $2\times10^6$ PBLs were stimulated with anti-CD2/anti-CD3/anti-CD28 as described under "Materials and Methods" and co-cultured with different concentrations of exo-hASCs (4, 8, and 16 μg/106 PBLs) during 6 days. The proliferation ability was determined by CFSE dilution. Non-stimulated PBLs were used as negative control, and stimulated PBLs without exosomes constituted the positive control. As expected, the proliferation rate of non-stimulated PBLs was very low (data not shown) and the maximum proliferation rate was reached by stimulated PBLs without exosomes. A total of eight cell divisions were detected by CFSE fluorescence. As shown in the FIG. 2A, when in vitro stimulated lymphocytes were cultured in the presence of different concentrations of exo-hASCs, the proliferation rate was proportionally decreased both in CD4+ and CD8+ T cells. A large percentage of cells presented a low number of cell divisions, while the highest number of cell divisions was reached by a lower percentage of cells. A detailed representation showing the percentage of cells in each division cycle is provided in the FIG. 2A. A representative histogram (FIG. 2B) and a detailed representation showing the percentage of cells in each division cycle is also provided (FIG. 2C).

Here, it can be seen how increasing concentrations of exosomes are arresting both CD4 and CD8 proliferation from eight generations to seven. Moreover, exosomes are retaining the cells in the earlier division cycles 4, 5, and 6, in where the percentage of cells is significantly higher in the presence of exosomes, however, division cycles 7 and 8 have a significantly reduced percentage of cells when higher doses of exosomes were used. The first two division cycles contain a very low percentage of T cells both in the presence or absence of exosomes, indicating that the effect of the polyclonal stimulation starts after these two division cycles; nevertheless the presence of exosomes is still significantly retaining cells in these first two division cycles (although this is happening in a group of T cells below 10%). The statistical analysis showed significant differences in different division cycles either in CD4+ and CD8+ T cells. Finally, the stimulation index was calculated on CD4+ and CD8+ T cells as frequencies of CFSE-low T cells among unstimulated T cells. The stimulation index of CD4+ and CD8+ T cells stimulated with anti-CD2/anti-CD3/anti-CD28 was 692.3 and 655.6, respectively. However, when PBLs were stimulated in the presence of exosomes, the stain index significantly decreased on CD4+ T cells (589.93±39.31, 585±80.27, 529.14±58.88 at 4, 8, and 16 μg) as well as in CD8+ T cells (519.75±60.97, 488.03±107.32, 437.4±79.25 at 4, 8, and 16 μg).

Figure 3:
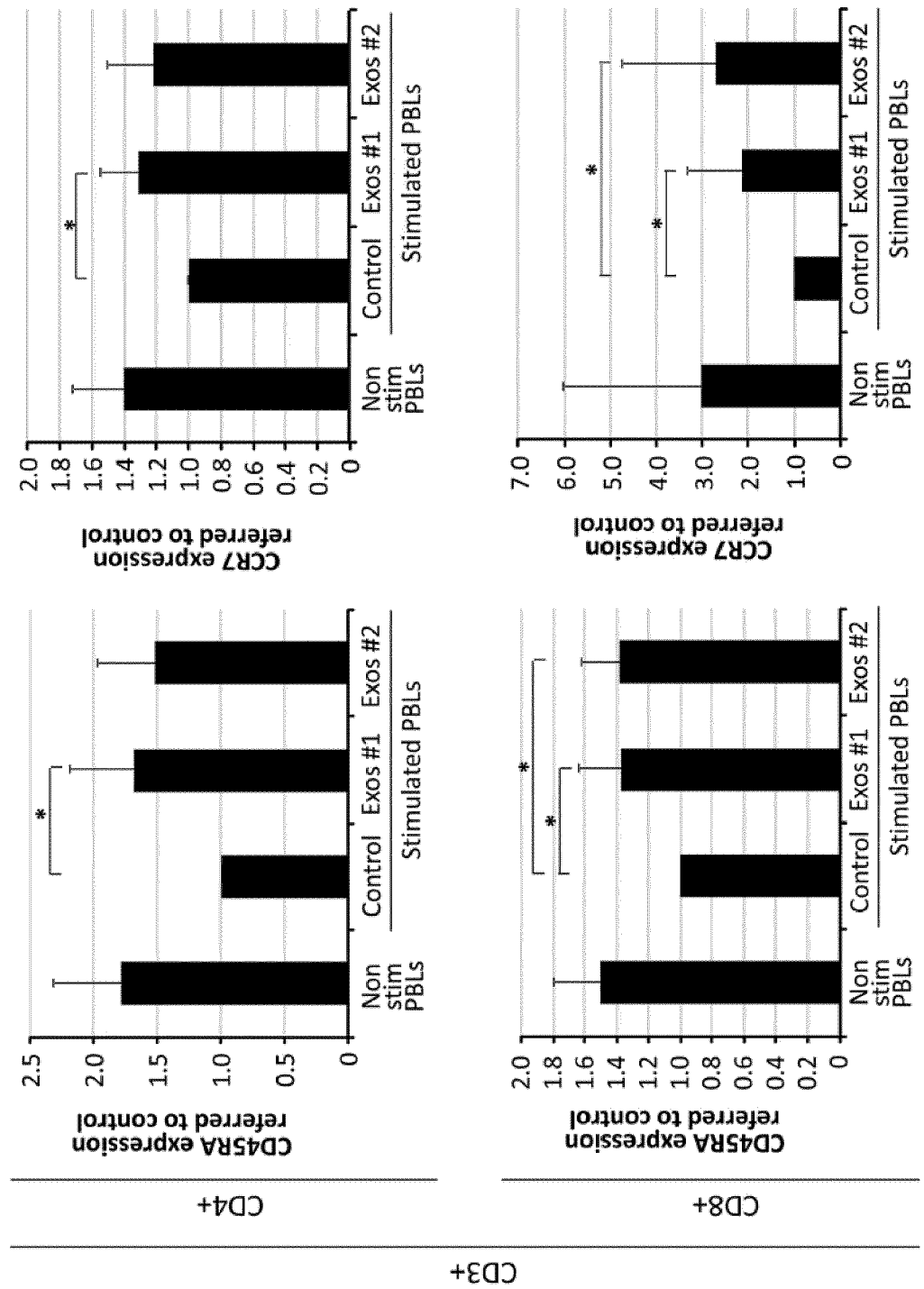
FIG. 3. Percentage of CD45RA and CCR7 expression on in vitro stimulated T cells co-cultured in the presence of exo-hASCs. At day 6, in vitro stimulated PBLs were analyzed for CD45RA and CCR7 on CD8$^+$ and CD4$^+$ T cell subsets. Two different exo-hASCs at 16 mg/10$^6$ cells from different donors were used in these experiments (Exos #1 and Exos #2). The graphs show the normalized quantitative expression referred to control (in vitro stimulated T cells in the absence of exo-hASCs). Values shown in the bars represent mean±SD of three independently performed experiments. Horizontal bars represent statistically significant differences between the stimulated PBLs groups (significant at p±0.1).

T Cells Subsets Distribution of In Vitro Stimulated T Cells Co-Cultured in the Presence of Exo-hASCs The CD45RA isoform and the chemokine receptor CCR7 are surface markers commonly used to identify the differentiation stages of CD4+ and CD8+ T cells. In order to study the effect of exo-hASCs over lymphocyte subsets, a total of 2×106 stimulated PBLs were cultured in the presence of exo-hASCs (from two different donors) at 16 μg/106 PBLs. At day 6, flow cytometry was performed using a commercial antibody against CD45RA and CCR7. The quantitative expression of CD45RA and CCR7 was normalized referred to control (in vitro stimulated T cells in the absence of exo-hASCs). The results showed a significant decrease CD45RA+ and CCR7+ cells both in the CD4+ and CD8+ T cells in the positive control (stimulated PBLs). However, the loss of CD45RA and CCR7 on in vitro stimulated PBLs was partially compensated by the presence of exo-hASCs (FIG. 3).

Figure 4:
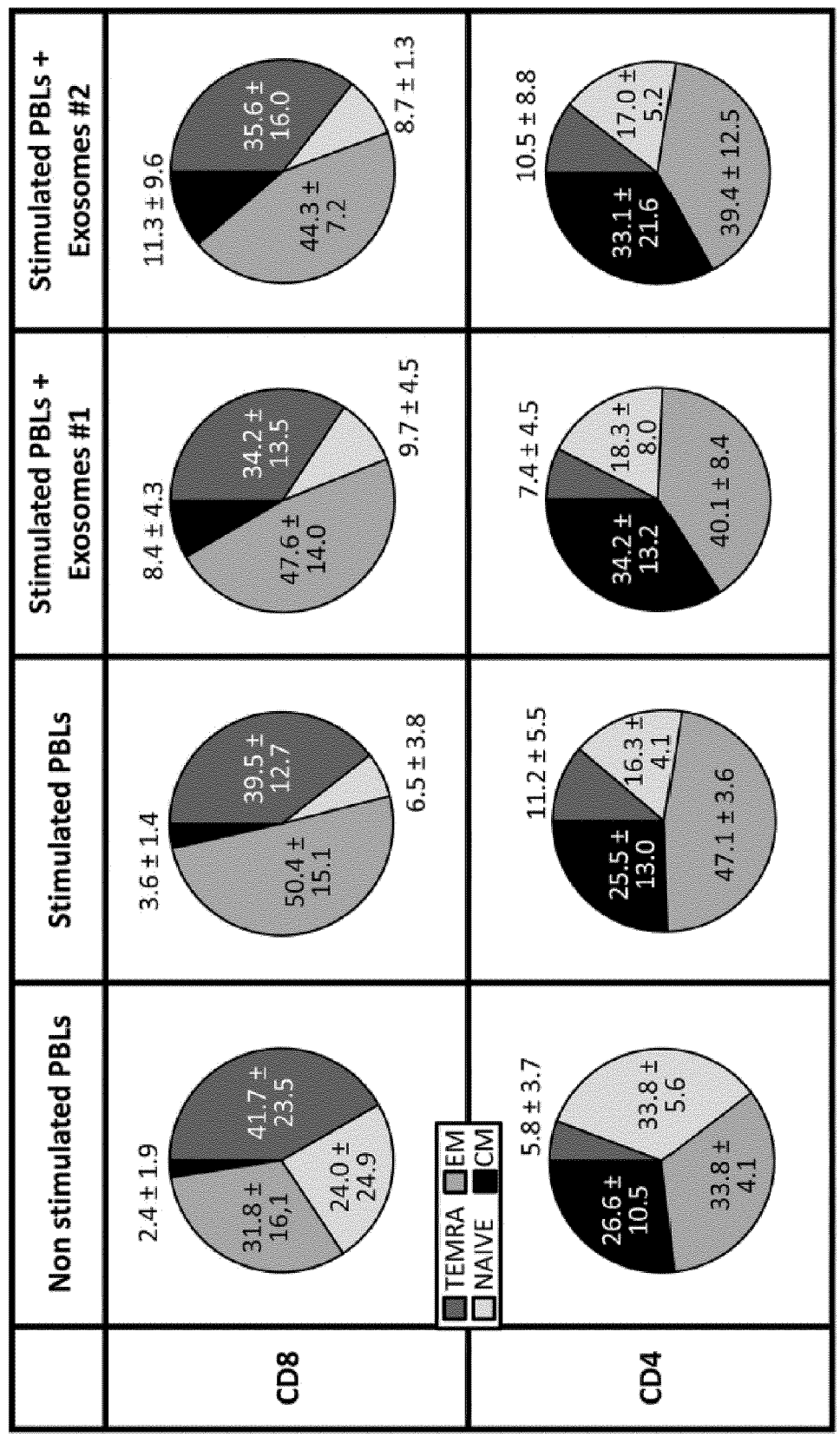
FIG. 4. CD45RA and CCR7 co-expression on in vitro stimulated T cells co-cultured in the presence of exo-hASCs. At day 6, in vitro stimulated PBLs were analyzed for the co-expression of CD45RA and CCR7. The CD45RA isoform and CCR7 distinguishes four subsets of T cells: terminally differentiated RA$^+$ T cells (TEMRA, CD45RA$^+$ CCR7$^-$), naïve T cells (NAIVE, CCR7$^+$ CD45RA$^+$), and two memory subsets: effector memory (EM, CD45RA$^-$ CCR7$^-$) and central memory (CM, CD45RA$^-$ CCR7$^+$). Two different exosomes from different donors were used in these experiments (Exos #1 and Exos #2). Values shown represent mean±SD of 3 independently performed experiments.

In the model proposed by Lanzavecchia and Sallusto, four different stages have been defined within CD8+ T cells according to the combined analysis of CD45RA and CCR7 expression, namely: naïve (CD45RA$^+$ CCR7$^+$), central memory (CD45RA CCR7$^+$) and at least two subset of effector-memory cells: effector-memory cells (CD45RA$^-$ CCR7$^-$) and terminally differentiated effector-memory cells (CD45RA$^+$ CCR7−) (Geginat J, Lanzavecchia A and Sallusto F. Blood (2003) 101:4260-6). To study the effect of exo-hASCs over this distribution, the co-expression of CD45RA and CCR7 was analyzed by flow cytometry on CD4$^+$ and CD8+ T cell subsets. As shown in FIG. 4, although the percentage of naïve cells was not significantly modified by the presence of exo-hASCs, a significant decrease of terminally differentiated effector-memory cells (CD45RA$^+$ CCR7$^-$) was observed on in vitro stimulated CD8$^+$ T cells cultured in the presence of exo-hASCs. In the case of CD4+ T cells, exo-hASCs reduced the percentage of effector-memory cells (CD45RA$^-$ CCR7$^-$) and significantly increased the percentage of central memory cells (CD45RA$^-$ CCR7$^+$).

These results evidenced that exo-hASCs hamper the in vitro differentiation mediated by anti-CD3/CD2/CD28 stimuli. Actually, in the case of CD8+ and CD4+ T cells, exo-hASCs have an inhibitory effect in the differentiation of toward a terminally differentiated phenotype and effector-memory phenotype, respectively.

Figure 5:
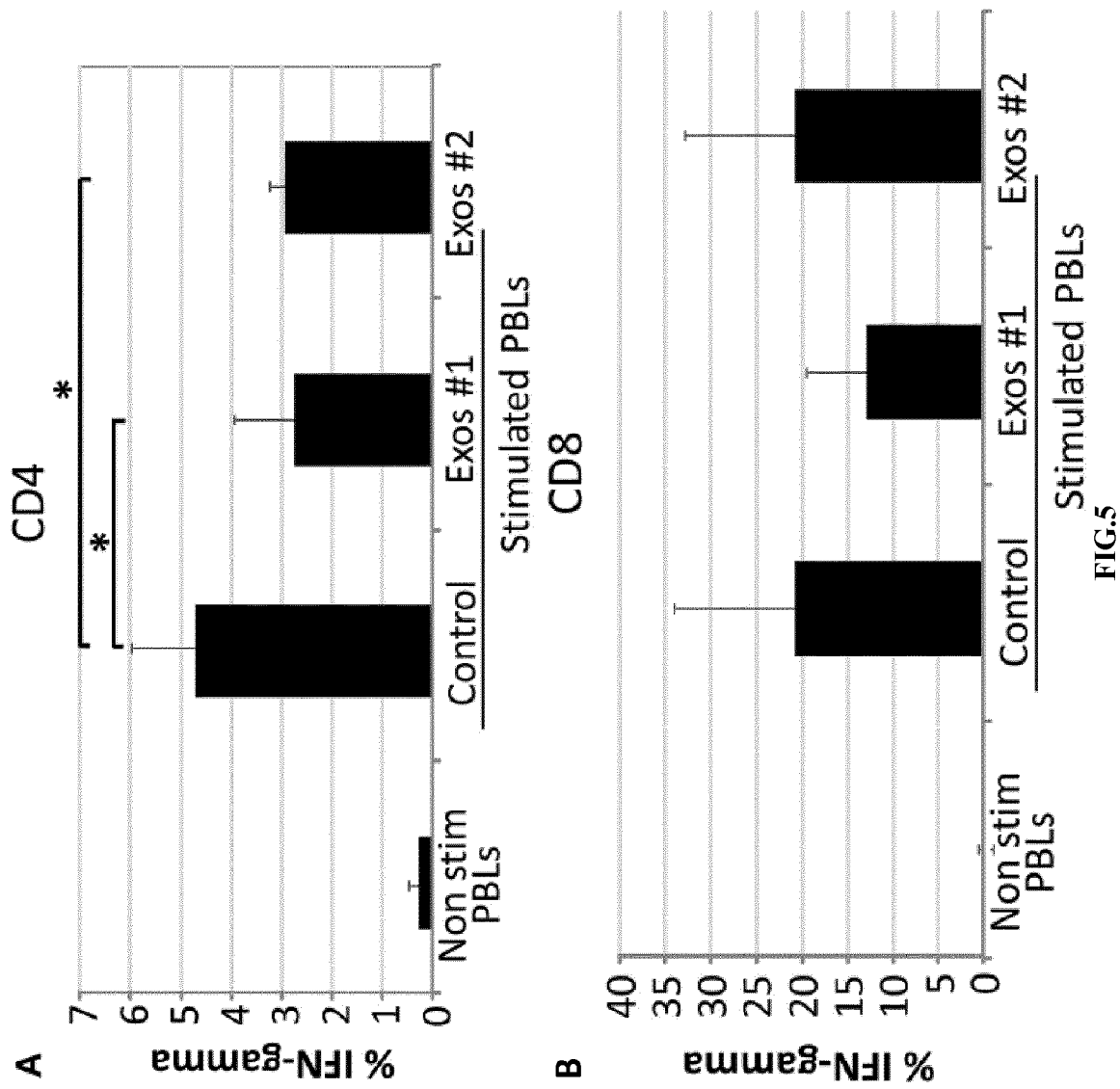
FIG. 5. The exo-hASCs inhibit the IFN-γ production of in vitro stimulated T cells. Two different exosomes from different donors were used in these experiments (Exos #1 and Exos #2). Graphs represent the mean±SD of 3 independently performed experiments. A representative dot plot of each condition is represented below each graph, and numbers in the quadrants indicate the percentage of IFN-γ in gated CD4$^+$ (A) and CD8$^+$ T cells (B) (significant at p±0.05).
Figure 8:
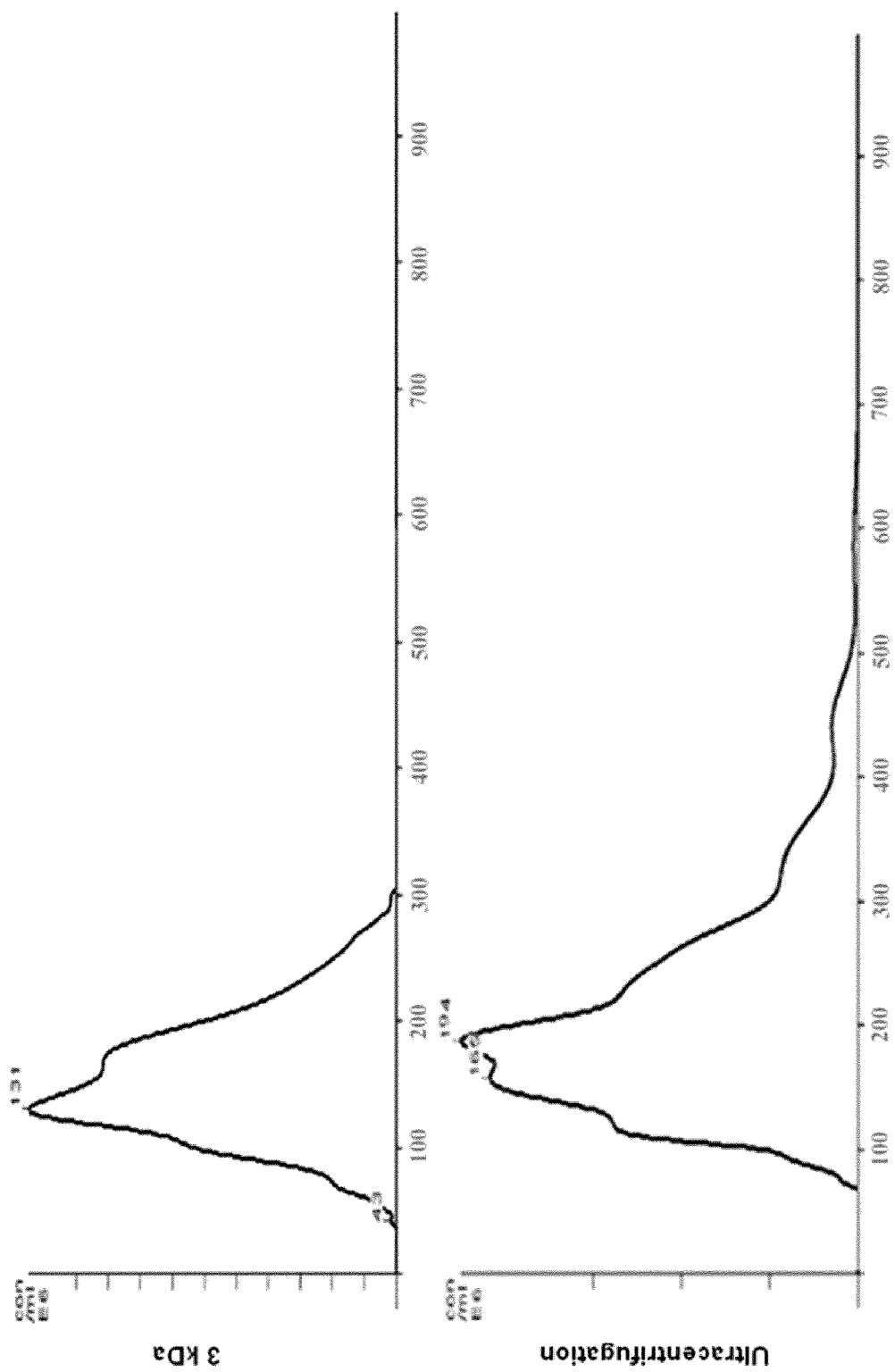
FIG. 8 Representative figures of particle sizes from different samples. The size of the particles was determined by NanoSight. The X axis scale refers to 100 nm per division. The scale of the Y axis represents the particle concentration expressed in particles per ml.
Figure 9:
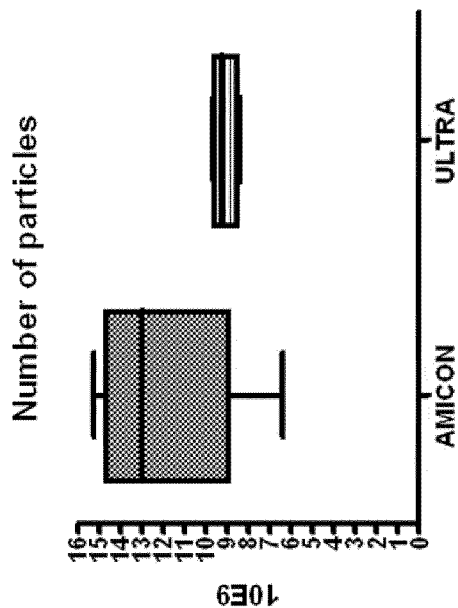
FIG. 9.—Determination of particle number from different samples. The number of particles in the enriched fraction exosomes was determined by NanoSight.
Figure 10:
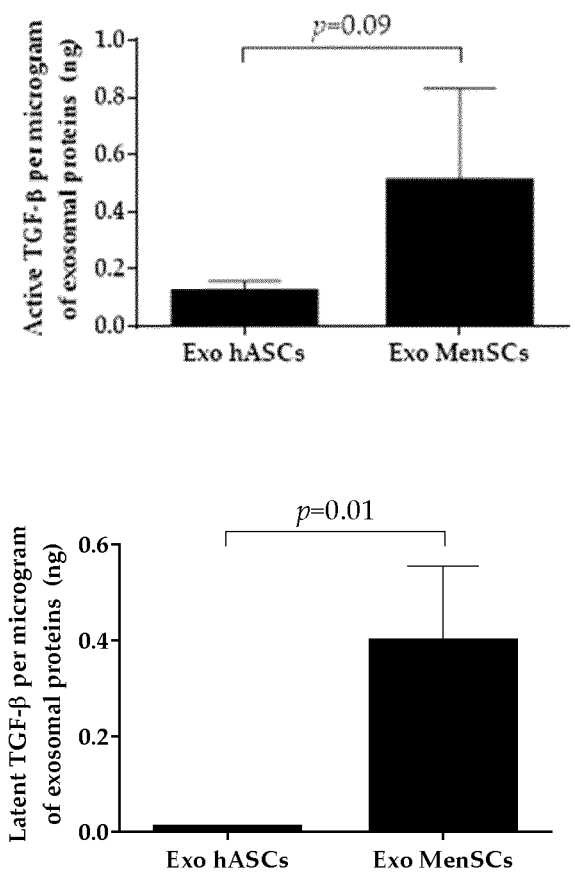
FIG. 10.—Analysis of different exosomes by TGF-β1 ELISA. Mean and standard deviation of the different donor exosomes are represented for Exo hASC (n=3) and for exo MenSC (n=4). Samples were analyzed after acid treatment by TGF-β1 ELISA and without acid treatment by LAP ELISA

IFN-γ Production on In Vitro Stimulated T Cells Co-Cultured in the Presence of Human Adipose Mesenchymal Stem Cells Derived Exosomes The IFN-γ is a pro-inflammatory cytokine secreted by immune cells under certain conditions of activation. There is a direct correlation between IFN-γ secretion and the level of T cell activation. In order to determine the effect of exosomes on the secretory IFN-γ response of T cells, PBLs were cultured in the presence and absence of exo-hASCs during 6 days and intra-cellular levels of IFN-γ were determined on CD4+ and CD8+ T cell subsets. Our results showed that, at day 6, the percentage of intracellular IFN-γ was reduced when PBLs were cultured with exosomes, in comparison to positive control, in both T cell subsets. However, this reduction was only statistically significant on gated CD4+ T cells (FIG. 5). These results demonstrated that exo-hASCs impaired not only the differentiation phenotype of lymphocytes but also their IFN-γ secretion.

Considering that IFN-γ is crucial for protection against immune-mediated inflammatory disorders, it could be assumed that exo-hASCs could be used as ideal vehicles for a local immunosuppression. Moreover, in contrast to cell therapy, where the viability, homing, or implantation of individual cells is compromised, the usage of well-characterized exo-hASCs in a dosing regimen that can be controlled and defined in space and time could be considered an advantage. Additionally, several authors have reported the susceptibility of allogeneic cells to CD8+ T cells and NK cells, which is an important issue for the clinical efficacy of MSCs. In the case of exo-hASCs, these microvesicles will not be affected by cell-mediated lysis, which is an advantage for their therapeutic effectiveness.

Example 2

Exosomes are microvesicles derived from exocytosis of cells. They are secreted by different cell types and can be isolated both in cell culture supernatants and biological fluids. Exosomes derived from mesenchymal stem cells have an enormous therapeutic potential, promoting tissue regeneration and reducing inflammation. It has been shown that exosomes are involved in intercellular relationships allowing the exchange of proteins and lipids produced by cells and target cells. Exosomes contain RNA, micro-RNA and proteins from their cells of origin, which makes them an important signaling mechanism in physiological processes.

There are different methods for the isolation of exosomes, although the most common method is the ultracentrifugation. Given the enormous interest that has emerged from preclinical trials, the design of new isolation protocols of exosomes is currently a need in clinical settings. The objective of this study was to compare, in terms of yield, purity and size, different methods of isolation from human MSCs. Our results demonstrated that concentrator filters could be a promising alternative to conventional protocols in the isolation of exosomes from cell culture supernatants.

Materials and Methods

Human Mesenchymal Stem Cells were isolated from lipoaspirates obtained from human adipose tissue from healthy adult donors. Cells were seeded onto tissue culture flasks and expanded at 37° and 5% $CO_2$, changing the culture medium every 3-4 days.

For supernatant collection, when cells reached 80% confluence the culture medium was replaced by exosome isolation medium (DMEM without serum, containing 1% Insulin-Transferrin-Selenium). After 6 days in culture, supernatants were collected and centrifuged at 1000×g (10 min) and 5000×g (20 min) at 4° C. to eliminate cells and debris. The supernatants were also filtered by 0.45 μM and 0.22 μM filters. Finally, for the enrichment of exosomes, supernatants were centrifuged in a concentrator of 3 kDa of MWCO (molecular weight cut off) or ultracentrifuged at 100,000×g for 6 hours.

Exosome concentrations were measured by protein quantification in a Bradford assay. To quantify protein concentration, 20 μl of exosome samples were incubated with 180 μl of Bradford Reagent at room temperature. Absorbance was read at 595 nm, and protein concentration was extrapolated from a standard concentration curve of Bovine Serum Albumin.

The concentration and size of purified exosomes was measured by nanoparticle tracking analysis (NanoSight), which relates the rate of Brownian motion to particle size. Results were analyzed using the nanoparticle tracking analysis software package. Triplicate samples were diluted 1:10 in sterile-filtered PBS and analyzed.

Results

The ultracentrifugation method allowed the inventors to concentrate the supernatants between 65 and 70 times, while using 3 kDa filters the supernatants could be concentrated 100 times.

The resulting volume was used to determine total protein concentration by the Bradford method. It was observed that using 3 kDa concentrators the protein concentration was 5.8 times higher than by ultracentrifugation. The 3 kDa concentrator resulted in a protein concentration of 490.43 μg/ml±121.03, while the ultracentrifugation resulted 90.40 μg/ml±57.16.

The enriched supernatants were the analyzed for particle size. It was observed that the particles isolated with the 3 kDa concentrator were smaller than particles isolated by ultracentrifugation. The particles obtained with the 3 kDa concentrator had an mean size of 191.08 nm±13.48, while the particles isolated by ultracentrifugation method was 246.83 nm±25.06.

Finally, the number of particles was higher when using the 3 kDa concentrator than with ultracentrifugation. The number of particles using the 3 kDa concentrator was $11.86 \times 10^9$ particles/ml±3.46, while the number of particles isolated with the ultracentrifugation method was $9.11 \times 10^9$ particles/ml±0.53.

CONCLUSIONS

1. The use of concentrator filters with smaller pore size and centrifuged at lower speeds allowed obtaining high amounts of exosomes with smaller sizes and higher purities.
2. Ultracentrifugation method for isolating exosomes resulted in a lower concentration and purity.
3. A favorable aspect of using concentration filters resides in the usage of conventional equipment which is commonly available in clinics, hospitals and research centers.

Example 3

Materials and Methods

Human Adipose Mesenchymal Stem Cells Isolation and Expansion

The human adipose mesenchymal stem cells (hASCs) were isolated from lipoaspirates obtained from human adipose tissue from healthy adult donors. Lipoaspirates were washed with PBS, and digested with collagenase type I in PBS. The digested sample was washed with 10% of fetal bovine serum (FBS), treated with ammonium chloride 160 mM, suspended in culture medium (DMEM containing 10% FBS), and filtered through a 40 μm nylon mesh. Cells were seeded onto tissue culture flasks and expanded at 37° C. and 5% $CO_2$, changing the culture medium every 7 days. Cells were passed to a new culture flask when cultures reached 90% of confluence. In addition, hASCs were tested by flow cytometry using specific surface markers being negative for CD14, CD31, CD34, CD45 and positive for CD29, CD59, CD90, and CD105 (data not shown). Cell lines from two healthy donors were used in the study. The biological samples were obtained after informed consent under the auspices of the appropriate Research and Ethics Committees.

Isolation and Purification of Exosomes from hASCs

An enriched fraction of exosomes from hASCs (exo-hASCs) was obtained from hASCs cultured in 175 cm2 flasks. When cells reached a confluence of 80%, culture medium (DMEM containing 10% FBS) was replaced by exosome isolation medium (DMEM containing 1% insulin-transferrin-selenium). The hASCs supernatants were collected every 3-4 days. Exosomes were isolated from supernatants were centrifuged at 1000×g for 10 min and 5000×g for 20 min at 4° C. to eliminate dead cells and debris. These supernatants were sequentially filtered using sterile cellulose acetate filter 0.45 μm and 0.20 μm. Finally, pre-filtered supernatants were concentrated in a Amicon® Ultra Centrifugal Filters, 3000 MWCO (Merck Millipore) at 4000×g for 1 hour at 4° C. The concentrated exosomes remained at the top of the concentrator and were stored at −20° C.

Characterization of Exo-hASCs

The concentration and size of purified exosomes were measured by nanoparticle tracking analysis (NanoSight Ltd, Amesbury, UK) that relates the rate of Brownian motion to particle size. Results were analyzed using the nanoparticle tracking analysis software package version 2.2. Triplicate samples were diluted 1:10 in sterile-filtered PBS and analyzed.

Isolation and Purification of Exosomes from menSCs (Menstrual Tissue)

An enriched fraction of exosomes from menSCs (exo-menSCs) was obtained from menSC cultured in 175 cm2 flasks. menSC were obtained from menstrual tissue. When cells reached a confluence of 80%, culture medium (DMEM containing 10% FBS) was replaced by exosome isolation medium (DMEM containing 1% insulin-transferrin-selenium). The menSC supernatants were collected every 3-4 days. Exosomes were isolated from supernatants were centrifuged at 1000×g for 10 min and 5000×g for 20 min at 4° C. to eliminate dead cells and debris. These supernatants were sequentially filtered using sterile cellulose acetate filter 0.45 μm and 0.20 μm. Finally, pre-filtered supernatants were concentrated in a Amicon® Ultra Centrifugal Filters, 3000 MWCO (Merck Millipore) at 4000×g for 1 hour at 4° C. The concentrated exosomes remained at the top of the concentrator and were stored at −20° C.

Characterization of Exo-menSCs

The concentration and size of purified exosomes were measured by nanoparticle tracking analysis (NanoSight Ltd, Amesbury, UK) that relates the rate of Brownian motion to particle size. Results were analyzed using the nanoparticle tracking analysis software package version 2.2. Triplicate samples were diluted 1:10 in sterile-filtered PBS and analyzed.

Bradford Assay

Exosome concentrations were indirectly measured by protein quantification in a Bradford assay. To quantify protein concentration, 20 μL of exosomes sample were incubated with 180 μL of Bradford reagent (Bio Rad Laboratories, Hercules, CA) at RT. Absorbance was read 5 min after at 595 nm, and protein concentration was extrapolated from a standard concentration curve of Bovine Serum Albumin TGFbeta Concentrations Active and latent TGF β forms were measured using the ELISA kits and following manufacturer instructions: Legend Max™ Free active TGF-β1 (Cat No 437707) and Legend Max™ Latent TGF-β (Cat No 432907).

Results

Exosomes obtained from different donor eASCS (ASC Donor 10, ASC Donor 13, ASC donor 14) and exosomes obtained from different donor menSC (menSC01, menSC 02, menSC03 and menSC04) were selected for measurements of TGF-β. As it can be shown in the table below both active TGF-β and latent TGF-β were detected in all the samples. TGF-β levels were much higher in the ExoMenSC than in the Exo hASCs

TABLE 2

Analysis of different exosomes by TGF-β1 ELISA. Mean and standard deviation of the differen donor exosomes are represented for Exo hASC (n = 3) and for exo MenSC (n = 4). Samples were analyzed after acid treatment by TGF-β1 ELISA and without acid treatment by LAP ELISA.

| Exo hASC D10 | Exo hASC D13 | Exo hASC D14 | Exo MenSC 01 | Exo MenSC 02 | Exo MenSC 03 | Exo MenSC 04 |
|---|---|---|---|---|---|---|
| ACTIVE TGF-β per microgram of exosome (ng) | | | | | | |
| 1.34E−01 | 8.58E−02 | 1.52E−01 | 6.68E−01 | 2.57E−01 | 8.87E−01 | 2.29E−01 |
| latent TGF-β per microgram of exosome (ng) | | | | | | |
| 9.12E−03 | 1.13E−02 | 8.20E−03 | 1.83E−01 | 5.56E−01 | 4.16E−01 | 4.39E−01 |

According to the low levels of TGF-β found in exo-hASCs (uniquely compared to exo-menSCs), these results may indicate that the immunomodulatory activity of exo-hASCs would be mediated by other paracrine-released molecules different to TGF-β. In contrast, the immunomodulatory effect of exo-menSCs (unpublished results) would be mediated by the TGF-β associated to exosomes.

TGF-β blocking experiments using exosomes together with in vitro activated lymphocytes will be performed to determine the relative inhibitory effect of TGF-β linked to exosomes. In these experiments, the anti-TGF-β blocking antibody (MA1-24734, clone 9016.2 at 1 µg/ml will be added to in vitro stimulated T cells co-cultured in the presence of exosomes.

The advantage of having exosomes with a comparable modulatory role for the immune cells but that do not use TGF-β as key paracrine factor for modulation could be considered as an advantage for those patients that might require the modulatory action of the exosomes but are under treatment with TGF-β inhibitors.

The invention claimed is:

1. A method of treating an immune-mediated inflammatory disease in a subject suffering from said disease, wherein the immune-mediated inflammatory disease is an inflammatory disease characterized by chronic inflammation and the immune-mediated inflammatory disease is selected from the group consisting of rheumatoid arthritis (RA), Inflammatory Bowel Disease (IBD), and Crohn's disease and wherein the method comprises administering to said subject a therapeutically effective amount of an isolated exosome population derived from MSCs, wherein the MSCs are adipose tissue-derived stem cells (ASCs) characterized in that:
the exosomes from said population comprise TSP-1.

2. The method according to claim 1, wherein the MSCs are allogeneic.

3. The method according to claim 1, wherein the isolated exosome population is administered systemically or locally.

4. The method according to claim 1 wherein the isolated exosome population is administered via the rectal, nasal, buccal, vaginal, subcutaneous, intracutaneous, intravenous, intraperitoneal, intramuscular, intraarticular, intrasynovial, intrasternal, intrathecal, intralesional, or intracranial route, or via an implanted reservoir.

5. The method according to claim 1, wherein the exosome population is administered in conjunction with at least one additional therapeutic agent.

* * * * *